(12) United States Patent
Adang

(10) Patent No.: US 6,534,495 B1
(45) Date of Patent: Mar. 18, 2003

(54) SERINE PROTEASE INHIBITORS

(75) Inventor: Anton Egbert Peter Adang, Eindhoven (NL)

(73) Assignee: Akzo Nebel, Arnhem (NL)

( * ) Notice: Subject to any disclaimer, the term of this patent is extended or adjusted under 35 U.S.C. 154(b) by 0 days.

(21) Appl. No.: 09/403,856

(22) PCT Filed: Apr. 28, 1998

(86) PCT No.: PCT/EP98/02587

§ 371 (c)(1), (2), (4) Date: Oct. 26, 1999

(87) PCT Pub. No.: WO98/50420

PCT Pub. Date: Nov. 12, 1998

(30) Foreign Application Priority Data

May 2, 1997 (EP) .............................................. 97201286

(51) Int. Cl.⁷ .......................... C07K 5/078; A61K 38/04
(52) U.S. Cl. ............................ 514/212.03; 514/212.08; 514/309; 514/349; 514/550; 540/524; 540/527; 546/141; 546/297; 560/13; 560/150
(58) Field of Search ................................ 540/524, 527; 546/297, 141; 560/13, 150; 514/212.03, 212.08, 309, 349, 550

(56) References Cited

U.S. PATENT DOCUMENTS 6,432,921 B2 * 8/2002 Adang et al. .................. 514/18
2001/0007764 A1 * 7/2001 Adang et al. ................ 435/184

FOREIGN PATENT DOCUMENTS

| EP | 195212 | * | 9/1986 |
| WO | WO 96/40743 | | 12/1996 |
| WO | WO 97/17363 | * | 5/1997 |
| WO | WO 98/09987 | * | 3/1998 |

OTHER PUBLICATIONS

Rauch et al. PubMed Abstract (Ann Intern Med, 134(3): 224–38), 2001.*

Van Aken et al., PubMed Abstract (Clin Appl Thromb Hemost, 7(3): 195–204), 2001.*

Jones et al, *J. Enzyme Inhib.*, vol. 9:43–60, 1995.

* cited by examiner

*Primary Examiner*—Deepak Rao
(74) *Attorney, Agent, or Firm*—Mark W. Milstead

(57) ABSTRACT

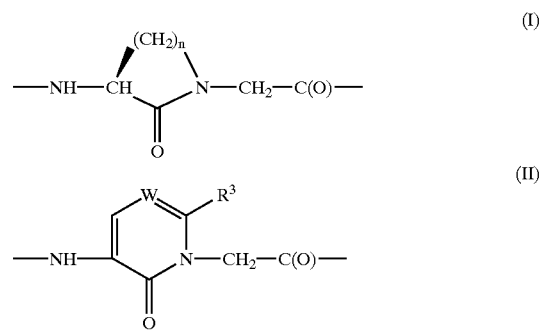

The invention relates to a compound having the formula (I): $R^1SO_2$—B—X—Z—C(O)—Y, B is a bond, an amino acid of the formula —NR—CH[$(CH_2)_pC(O)OH$]—C(O)— or an ester derivative thereof wherein p is 1, 2, or 3, Gly, D-1-Piq, D-3-Piq, D-1-Tiq, D-3-Tiq, D-Atc, Aic, or a L- or D-amino acid having a hydrophobic, basic or neutral side chain; X is an amino acid with a hydrophobic side chain, glutamine, serine, theronine, a cyclic amino acid optionally containing an additional heteroatom selected from N, O or S, and optionally substituted with (1–6C)alkyl, (1–6C)alkoxy, benzyloxy or oxo, or X is 2-amino-isobutyric acid, —$NR^2$—$CH_2$—C(O)— or the fragment (I) or (II), wherein n is 2, 3, or 4, W is CH or N and $R^3$ is H, (1–6C)alkyl or phenyl which groups may optionally be substituted with hydroxy, (1–6C)alkoxy, COOH, COO(1–6C)alkyl, $CONH_2$, or halogen; Z is lysine or 4-aminocyclohexylglycine. The compounds of the invention have anticoagulant activity and can be used in treating or preventing thrombin-related diseases. The variable $R^1$ and Y are defined in claim 1.

10 Claims, No Drawings

SERINE PROTEASE INHIBITORS

FIELD OF THE INVENTION

The invention relates to new serine protease inhibitors, pharmaceutical compositions containing the same, as well as to the use of said inhibitors for the manufacture of a medicament for treating and preventing thrombin-related diseases.

BACKGROUND OF THE INVENTION

Serine proteases are enzymes which, amongst other things, play an important role in the blood coagulation cascade. Members of this group of proteases are for example thrombin, trypsin, factors VIIa, IXa, Xa, XIa, XIIa, and protein C.

Thrombin is the serine protease which regulates the last step in the coagulation cascade. The prime function of thrombin is the cleavage of fibrinogen to generate fibrin monomers, which form an insoluble gel by cross-linking. In addition, thrombin regulates its own production by activating factors V and VIII earlier in the cascade. It also has important actions at the cellular level, where it acts on specific receptors to cause platelet aggregation, endothelial cell activation and fibroblast proliferation. Thus thrombin has a central regulatory role in haemostasis and thrombus formation. Since inhibitors of thrombin may have a wide range of therapeutical applications, extensive research has been performed in this area. In the development of synthetic inhibitors of serine proteases, and more specifically of thrombin, the interest in small synthetic peptides that are recognized by proteolytic enzymes in a manner similar to that of natural substrates, has increased. As a result, new peptide-like inhibitors have been prepared, such as the transition state inhibitors of thrombin.

The search for more effective and more selective thrombin inhibitors continues unabated in order to obtain thrombin inhibitors which can be administered in lower dosages and which have fewer and less severe side effects. Furthermore, special attention is paid to oral bioavailability. Potent intravenous thrombin inhibitors are clinically effective in acute care settings requiring the treatment of thrombin-related diseases. However, particularly the prevention of thrombin-related diseases such as myocardial infarct, thrombosis and stroke require long-term therapy, preferably by orally dosing an anticoagulant.

Many of the peptide-like serine protease inhibitors, in particular thrombin inhibitors, disclosed in prior publications are based on the sequence -D-Phe-Pro-Arg-, see for example compounds as disclosed by Brady et al. [Bioorganic & Medical Chemistry, 3 (1995), 1063–78] and in U.S. Pat. No. 5,597,804. Thrombin inhibitors may also contain lysine side chains instead of arginine, such as other inhibitors disclosed by Brady et al., and Lewis et al. [Thrombosis and Haemostasis, 74(4) (1995), 1107–12], and further by Jones et al. [J. Enzyme Inhibition, 9 (995), 43–60]. In the latter publication it was reported that tripeptide compounds containing α-keto methyl ester functions are labile compounds and therefore unfavourable for further development as thrombin inhibitors. Also thrombin inhibitors having an aminocyclohexyl moiety instead of lysine or arginine side chain are known [WO 94/25051]. From these and also other references [e.g. U.S. Pat. No. 5,523,308] a number of variations at the C-terminus of these peptide-like thrombin inhibitors is known. The developments in this field have already improved the understanding of how to modulate the biological properties of this type of thrombin inhibitors. However, although great effort is being spend on finding selective thrombin inhibitors having good oral bioavailability there are still few transition state thrombin inhibitors known in the art which fulfill these requirements.

SUMMARY OF THE INVENTION

Surprisingly, it has now been found that compounds of the formula:

$$R^1SO_2—B—X—Z—C(O)—Y \qquad (I)$$

wherein $R^1$ is $R^2OOC—(CHR^2)_m—$ or $R^2NH—CO—(CHR^2)_m—$ or is selected from (1–12C)alkyl, (2–12C)alkenyl, which groups may optionally be substituted with (3–12C)cycloalkyl, (1–6C)alkoxy, OH, $COOR^2$, $CF_3$ or halogen, and from (6–14C)aryl, (7–15C)aralkyl and (8–16)aralkenyl, the aryl groups of which may optionally be substituted with (1–6C)alkyl, (3–8C)cycloalkyl, (1–6C)alkoxy, OH, COOH, $CF_3$ or halogen;

m is 1, 2 or 3;

each group $R^2$ is independently H, (1–12C)alkyl, (3–8C)cycloalkyl, (6–14C)aryl or (7–1 5C)aralkyl, the aryl groups of which may be substituted with (1–6C)alkyl, (1–6C)alkoxy or halogen;

B is a bond, an amino-acid of the formula —NH—CH[(CH_2)_pC(O)OH]—C(O)— or an ester derivative thereof wherein p is 1, 2 or 3, Gly, D-1-Piq, D-3-Piq, D-1-Tiq, D-3-Tiq, D-Atc, Aic, or a L- or D-amino acid having a hydrophobic, basic or neutral side chain;

X is an amino acid with a hydrophobic side chain, glutamine, serine, threonine, a cyclic amino acid optionally containing an additional heteroatom selected from N, O or S, and optionally substituted with (1–6C)alkyl, (1–6C)alkoxy, benzyloxy or oxo, or X is 2-amino-isobutyric acid, $—NR^2—CH_2—C(O)—$ or the fragment

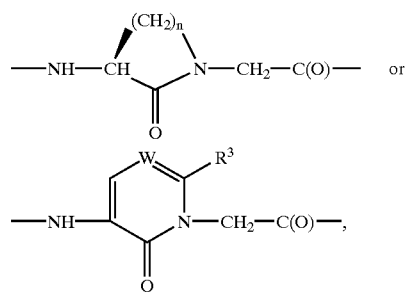

wherein n is 2, 3, or 4, W is CH or N and $R^3$ is H, (1–6C)alkyl or phenyl which groups may optionally be substituted with hydroxy, (1–6C)alkoxy, COOH, COO(1–6C)alkyl, $CONH_2$, or halogen;

Z is lysine or 4-aminocyclohexylglycine;

Y is $—NH-(1–6C)$alkylene-$C_6H_5$, the phenyl group of which may be substituted with (1–6C)alkyl, (1–6C)alkoxy or halogen, or Y is $—OR^4$ or $—NR^5R^6$, wherein $R^4$ is H, (2–6C)alkyl or benzyl, and $R^5$ and $R^6$ are independently H, (1–6C)alkoxy, or (1–6C)alkyl optionally substituted with halogen, or $R^5$ and $R^6$ together are (3–6C)alkylene, or $R^5$ and $R^6$ together with the nitrogen atom to which they are bonded are

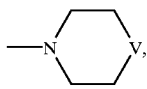

wherein V is O, S or $SO_2$;

or a prodrug thereof or a pharmaceutically acceptable salt thereof, are potent and selective serine protease inhibitors. Specifically, the compounds of the present invention are inhibitors of thrombin, of factor VIIa/tissue factor and of factor Xa. Compounds of the invention show improved pharmacokinetics, and in particular good bioavailability after oral administration. The α-(2–6C)keto ester compounds which are part of the present invention do not show the disadvantages of the previously reported labile α-keto methyl ester compounds.

The compounds of the present invention are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The compounds of the invention may also be used as anticoagulants in extracorporeal blood circuits, as necessary in dialysis and surgery. The compounds of the invention may also be used as in vitro anticoagulants.

DETAILED DESCRIPTION OF THE INVENTION

Preferred serine protease inhibitors according to this invention are the compounds wherein Z is lysine. More preferred are the compounds wherein X is a cyclic amino acid, an amino acid with a hydrophobic side chain, glutamine, serine, threonine, $-NR^2-CH_2-C(O)-$, or the fragment

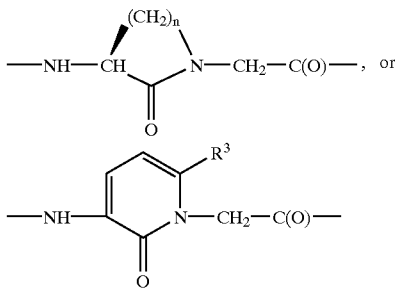

wherein $R^3$ is H, (1–6C)alkyl or phenyl.

Particularly preferred are the compounds wherein X is proline, leucine, glutamine, threonine, phenylalanine, $-NR^2-CH_2-C(O)-$ wherein $R^2$ is methyl, cyclopentyl or cyclohexyl, or the fragment

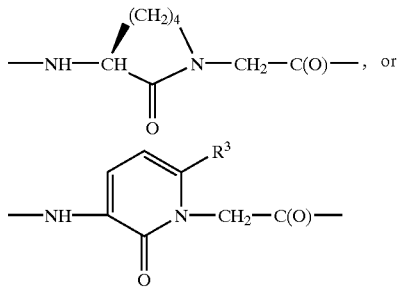

wherein $R^3$ is H or methyl.

Other preferred compounds are those wherein B is a bond or a D-amino acid having a hydrophobic or neutral side chain. The most preferred compounds of the invention are those wherein $R^1$ is (1–6C)alkyl or benzyl. Preferably $R^4$ in the definition of Y is (2–6C)alkyl or benzyl. In particular preferred are the compounds wherein Y is $-OCH(CH_3)_2$. Also preferred compounds have Y is $NH_2$.

The term (1–12C)alkyl means a branched or unbranched alkyl group having 1 to 12 carbon atoms, such as methyl, ethyl, t-butyl, isopentyl, heptyl, dodecyl, and the like. Preferred alkyl groups are (1–6C)alkyl groups, having 1–6 carbon atoms.

A (2–12C)alkenyl group is a branched or unbranched unsaturated hydrocarbon group having 2 to 12 carbon atoms. Preferred are (2–6C)alkenyl groups. Examples are ethenyl, propenyl, allyl, and the like.

The term (1–6C)alkylene means a branched or unbranched alkylene group having 1 to 6 carbon atoms, such as $-(CH_2)_s-$ and s is 1 to 6, $-CH(CH_3)-$, $-CH(CH_3)-(CH_2)-$, etc. Preferred alkylene groups in the definition of Y are ethylene and methylene.

The term (1–6C)alkoxy means an alkoxy group having 1–6 carbon atoms, the alkyl moiety of which has the meaning as previously defined.

The term (3–12C)cycloalkyl means a mono- or bicycloalkyl group having 3–12 carbon atoms which cycloalkyl group may optionally be substituted with an oxo group. Preferred are (3–8C)cycloalkyl, such as cyclopropyl, cyclobutyl, cyclopentyl, cyclohexyl, cycloheptyl, cyclooctyl, etc. Cyclopentyl and cyclohexyl are even more preferred cycloalkyl groups. A preferred cycloalkyl substituted alkyl group in the definition of $R^1$ is the camphor group.

A (6–14C)aryl group is an aromatic moiety of 6 to 14 carbon atoms. The aryl group may further contain one or more hetero atoms, such as N, S, or O. Examples of aryl groups are phenyl, naphthyl, (iso)quinolyl, indanyl, and the like.

(7–1 5C)Aralkyl and (8–16C)aralkenyl groups are alkyl and alkenyl groups respectively, substituted by one or more aryl groups, the total number of carbon atoms being 7 to 15 and 8 to 16, respectively.

The term halogen means fluorine, chlorine, bromine or iodine.

The term ester derivative means any appropriate ester derivative, preferably (1–4C)alkyl-esters, such as methyl-, ethyl- or t-butyl-esters.

The terms Atc means 2-aminotetralin-2-carboxylic acid and Aic means amino indane carboxylic acid. The terms 1- and 3-Tiq mean 1,2,3,4-tetrahydroisoquinoline-1- and -3-carboxylic acid, respectively; 1- and 3-Piq are perhydroisoquinoline-1- and -3-carboxylic acid, respectively.

The term amino acid having a hydrophobic side chain means an amino acid having a side chain being (3–8C)

cycloalkyl, (6–14C)aryl or (1–6C)alkyl, which alkyl group may optionally be substituted with one or more (3–8C) cycloalkyl groups or (6–14C)aryl groups. The hydrophobic side chain may optionally be substituted with one or more substituents, such as hydroxy, halogen, trifluoromethyl, —OSO$_2$CF$_3$, (1–4C)alkyl (for instance methyl or ethyl), (1–4C)alkoxy (for instance methoxy), phenyloxy, benzyloxy, and the like. Preferred amino acids with a hydrophobic side chain are leucine, valine, cyclohexylalanine, 4-methoxy-cyclohexylalanine, cyclo-octylalanine, phenylalanine, D-naphthylalanine, tyrosine, O-methyl tyrosine (or: p-methoxy-phenylalanine), 3,3-diphenylalanine, norleucine and leucine.

Amino acids having a basic side chain are for example, but not limited to, arginine and lysine, preferably arginine.

The term amino acids having a neutral side chain refers to amino acids such as glutamine (Gln), methionine sulfon, asparagine (Asn) and the like. Preferred are Gln and Asn.

Cyclic amino acids are for example 2-azetidine carboxylic acid, proline, pipecolic acid, 1-amino-1-carboxy-(3–8C) cycloalkane (preferably 4C, 5C or 6C), 4-piperidine carboxylic acid, 4-thiazolidine carboxylic acid, 3,4-dehydroproline, azaproline, 2-octahydroindole carboxylic acid, and the like. Preferred are 2-azetidine carboxylic acid, proline, pipecolic acid, 4-thiazolidine carboxylic acid, 3,4-dehydroproline and 2-octahydroindole carboxylic acid. In the definitions, the term substituted means: substituted by one or more substituents.

The invention also includes prodrugs of the compounds of formula I, which after administration are metabolized into the active compounds. Suitable prodrugs are for example N-alkoxycarbonyl protected (preferably N-ethoxycarbonyl) derivatives of the compounds of formula I.

The invention further includes a process for preparing a compound of formula I, comprising coupling of suitably protected amino acids or amino acid analogs, followed by removing the protective groups.

The compounds according to formula I may be prepared in a manner conventional for such compounds. To that end, suitably Nac protected (and side-chain protected if reactive side-chains are present) amino acid derivatives or peptides are activated and coupled to suitably carboxyl protected amino acid or peptide derivatives either in solution or on a solid support. Protection of the α-amino functions generally takes place by urethane functions such as the acid-labile tert-butyloxycarbonyl group (Boc), benzyloxycarbonyl (Cbz) group and substituted analogs or the base-labile 9-fluorenyl-methyloxycarbonyl (Fmoc) group. The Cbz group can also be removed by catalytic hydrogenation. Other suitable amino protective groups include Nps, Bpoc, Msc, etc. A good overview of amino protective groups is given is given in The Peptides, Analysis, Synthesis, Biology, Vol. 3 E. Gross and J. Meienhofer, Eds., (Academic Press, New York, 1981). Protection of carboxyl groups can take place by ester formation e.g. base-labile esters like methyl- or ethylesters, acid labile esters like tert-butylesters, or hydrogenolytically-labile esters like benzylesters. Protection of the side chain function of lysine or 4-aminocyclohexylglycine may be accomplished by using the aforementioned groups. Activation of the carboxyl group of the suitably protected amino acids or peptides can take place by the azide, mixed anhydride, active ester, or carbodiimide method, especially with the addition of catalytic and racemization-suppressing compounds like 1-hydroxybenzotriazole, N-hydroxysuccinimide, 3-hydroxy-4-oxo-3,4-dihydro-1,2,3-benzotriazine, N-hydroxy-5-nor-bornene-2,3-dicarboximide. See, e.g. The Peptides, Analysis, Synthesis, Biology (see above) and Pure and Applied Chem. 59(3), 331–344 (1987).

The compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulfonic acid, fumaric acid, succinic acid, tartaric acid, citric acid, benzoic acid, and ascorbic acid.

The compounds of this invention possess one or more chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The compounds of the invention may be administered enterally or parenterally, and for humans Preferably in a daily dosage of 0.001–100 mg per kg body weight, preferably 0.01–10 mg per kg body weight. Mixed with pharmaceutically suitable auxiliaries, e.g. as described in the standard reference, Gennaro et al., Remington's Pharmaceutical Sciences, (18th ed., Mack Publishing company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is further explained by reference to the following illustrative Examples.

General

Abbreviations

Et=ethyl
Bzl=benzyl
Boc=tert-butyloxycarbonyl
Cbz=benzyloxycarbonyl
Cha=cyclohexylalanyl
Pro=prolyl
Lys=lysyl
Acg=4-aminocyclohexyl glycyl
TFA=trifluoro acetic acid
Pac=phenylacetyl
Nps=nitrophenylsulfonyl
Bpoc=2-p-biphenylisopropyloxycarbonyl
Asp=aspartyl
Glu=glutamyl
Dpa=diphenylalanyl
H-Aad-OH=amino-adipic acid
Tyr(Me)=(O-methyl)-tyrosyl
Phe=phenylalanyl
Nal=naphthylen-2-yl-alaninyl H-3-Tiq-OH=1,2,3,4-tetrahydroisoquinoline-3-carboxylic acid
Msc=methylsulfonylethyloxycarbonyl
Teoc=2-(trimethylsilyl)ethoxycarbonyl
norLeu(cyclo)-Gly-OH=(S)-3-amino-2-oxo-hexahydro-1-azepineacetic acid
norVal(cyclo)-Gly-OH=(S)-3-amino-2-oxo-1-piperidineacetic acid Experimental The solvent systems used in HPLC are: A: 0.5 M phosphate buffer pH=2.1; B: water; C: acetonitrile/water 3/2 v/v.

Unless stated otherwise the retention times (Rt (LC)) were determined on an analytical HPLC Supelcosil LC-18-DB column (5 μm particles; 250×2.1 mm), which was eluted using a gradient (as specified) of solvent systems A, B and C at a flow rate of 0.25 ml/min at 35° C.

EXAMPLE 1

BzlSO$_2$-norLeu(cyclo)-Gly-LysΨ[COCO]-NHBzl

(a) Cbz-Lys(Boc)-OMe

To a solution of Cbz-Lys(Boc)-OH (28 g) in dichloromethane/methanol (9/1 v/v; 500 mL) was added 2-(1H-benzotriazol-1-yl)-1,1,3,3-tetramethyluronium tetrafluoroborate (23.6 g) and the solution was adjusted to pH 8 by addition of triethylamine. The reaction mixture was stirred for 2 hours at room temperature. The mixture was washed successively with cold 1N hydrochloric acid, water, 5% sodium hydrogencarbonate, and water and dried over sodium sulfate. The filtrate was evaporated and the residue was chromatographed on silica gel using ethyl acetate/heptane (1/4 v/v) as eluent. The factions containing Cbz-Lys(Boc)-OMe were pooled and evaporated. Yield: 29.1 g TLC: Rf=0.85, ethyl acetate/heptane=3/1 v/v on silica.

(b) Cbz-Lys (Boc)Ψ[cyanoacetate]

To a cold (−78° C.) solution of Cbz-Lys(Boc)-OMe (29.1 g) in dry dichloromethane (800 mL) was added dropwise diisobutylaluminium hydride (222 mL of 1M solution in hexane) keeping the reaction temperature below −70° C. The resulting solution was stirred at −78° C. for 1 hour and an aqueous 5% citric-acid solution (600 mL) was added to the reaction mixture. The two layer mixture was stirred at room temperature for 10 minutes, the layers were separated and the aqueous layer was extracted twice with dichloromethane. The combined dichloromethane layers were washed with water, dried over sodium sulfate and filtered. The filtrate was stirred under a nitrogen atmosphere and cooled on a icewater-bath. A solution of sodium cyanide (36.3 g) and benzyltriethyl ammonium chloride (4.2 g) in water (600 mL) was added. Under vigorous stirring acetic anhydride was added portionwise (2×9 mL) over a period of 30 min. The organic layer was separated and the aqueous layer was extracted twice with dichloromethane. The combined dichloromethane layers were washed with water, dried over sodium sulfate and evaporated in vacuo. The residue was purified by chromatography on silica (eluent heptane/ethyl acetate=1/1 v/v) to yield Cbz-Lys (Boc)Ψ[cyanoacetate] (26.3 g.).

TLC: Rf=0.60, dichloromethane/ethyl acetate=7/3 v/v on silica.

(c) Cbz-Lys(Boc)Ψ[CHOHCO]-OMe

A solution of Cbz-Lys(Boc)Ψ[cyanoacetate] (26.3 g.) in diethylether/methanol=3/1 v/v (600 mL) was cooled to −20° C. under a nitrogen atmosphere, and 66 g of gaseous hydrogen chloride was introduced keeping the temperature below −5° C. The reaction mixture was kept at 4° C. overnight. Water (100 mL) was added dropwise to the reaction mixture keeping the temperature below 5° C. After stirring for 16 h at room temperature the organic layer was separated and washed with water. The aqueous layer was saturated with sodium chloride and extracted with sec-butanol/dichloromethane=3/2 v/v. The organic phase was washed with brine, dried over sodium sulfate, filtered and evaporated in vacuo to give 25.4 g of the crude amine. The residue was taken up in N,N-dimethylformamide (400 mL), di-tert-butyl dicarbonate (16 g) was added and adjusted to pH 8 using triethylamine. The reaction mixture was stirred at room temperature overnight. The solvent was removed by evaporation at reduced pressure. The residue was dissolved in ethyl acetate, washed with water and brine successively, dried over sodium sulfate, filtered and evaporated in vacuo. The residue was purified by chromatography on silica (eluent: ethyl acetate/heptane=4/6 v/v ) to yield Cbz-Lys (Boc)Ψ[CHOHCO]-OMe (15.8 g).

TLC: Rf=0.75, ethyl acetate/pyridine/acetic acid/water=63/20/6/11 v/v/v/v on silica.

(d) Cbz-Lys(Boc)Ψ[CHOHCO]—OH

A stirred solution of Cbz-Lys(Boc)Ψ[CHOHCO]-OMe (2.0 g) in dioxane/water=7/3 v/v (50 mL) at room temperature was treated portionwise with a 2M sodium hydroxide solution (2.36 mL). After 1 hour the reaction mixture was diluted with water (100 mL), 2M hydrochloric acid was added until pH 2.0 and extracted with dichloromethane. The combined organic phases were washed with water, dried over sodium sulfate, filtered and concentrated in vacuo to yield Cbz-Lys(Boc)Ψ[CHOHCO]—OH (1.85 g).

TLC: Rf=0.65, ethyl acetate/pyridine/acetic acid/water=63/20/6/11 v/v/v/v on silica.

(e) Cbz-Lys(Boc)Ψ[CHOHCO]-NHBzl

To a stirred solution of Cbz-Lys(Boc)Ψ[CHOHCO]—OH (0.90 g) in N,N-dimethylformamide (10 mL) were added 1-hydroxybenzotriazole (HOBt, 444 mg), N-methylmorpholine (0.5 mL), benzylamine (282 mg) and 1-(3-dimethylaminopropyl)-3-ethylcarbodiimide hydrochloride (EDCI, 462 mg). After stirring for 16 hours at room temperature the reaction mixture was poured into water and this aqueous mixture was extracted with ethyl acetate. The ethyl acetate extract was washed with 1N hydrochloric acid, water, aqueous 5% sodium hydrogencarbonate and water, dried over sodium sulfate, filtered and concentrated in vacuo to yield Cbz-Lys(Boc)Ψ[CHOHCO]-NHBzl (1.0 g).

TLC: Rf=0.81, ethyl acetate/pyridine/acetic acid/water=163/20/6/11 v/v/v/v on silica.

(f) H-Lys(Boc)Ψ[CHOHCO]-NHBzl.HCl

To a solution of Cbz-Lys(Boc)Ψ[CHOHCO]-NHBzl (1.0 g) in methanol (25 mL) were added 10% palladium on activated carbon (100 mg) and 2M hydrochloric acid (1 mL) and this suspension was hydrogenated at atmospheric pressure for 1 hour at room temperature. The palladium catalyst was removed by filtration and the filtrate was concentrated in vacuo to yield H-Lys(Boc)Ψ[CHOHCO]-NHBzl.HCl (0.87 g).

TLC: Rf=0.15, ethyl acetate/pyridine/acetic acid/water=163/20/6/11 v/v/v/v on silica.

(g) N-Boc-L-α-Amino-ε-caprolactam

To a stirred solution of L-α-Amino-ε-caprolactam (10 g) in dioxane/water (2/1 v/v) (30 mL) was added 1N sodium hydroxide solution (7.8 mL) followed by di-t-butyl dicarbonate (18.8 g). The mixture was stirred for 16 hours at room temperature and concentrated in vacuo. The residue was dissolved in ethyl acetate and washed with water and brine, dried over sodium sulfate, filtered and evaporated in vacuo. The crude material was triturated by hexane, filtered and dried in vacuo to yield N-Boc-L-α-Amino-ε-caprolactam (16 g).

TLC: Rf=0.85, ethyl acetate/heptane 1/1 v/v on silica.

(h) Boc-norLeu(cyclo)-Gly-OMe

N-Boc-L-α-Amino-ε-caprolactam (10 g) was dissolved in dichloromethane (100 mL). At −20° C. a 1M solution of lithium bis(trimethylsilyl)amide in tetrahydrofuran/cyclohexane 1/1 v/v (1 equiv.) was added slowly and the mixture was stirred for 30 min. Methyl bromoacetate (4 mL) was subsequently added and the mixture was stirred for 2 hours at room temperature. Additional lithium bis(trimethylsilyl)amide in tetrahydrofuran/cyclohexane 1/1 v/v was added to force the reaction to completion. The mixture was diluted by dichloromethane and washed with 0.1N hydrochloric acid, water, 5% aqueous sodium hydrogencarbonate solution and brine, dried over sodium sulfate, filtered and evaporated in vacuo. The residue was purified by chromatography on silica gel (eluent: heptane/ethyl acetate 6/4 v/v) to yield 12 g Boc-norLeu(cyclo)-Gly-OMe.

TLC: Rf=0.55, ethyl acetate/heptane 6/4 v/v on silica.

(i) BzlSO$_2$-norLeu(cyclo)-Gly-OMe

Boc-norLeu(cyclo)-Gly-OMe (3 g) was dissolved in TFA/dichloromethane 1/1 v/v (30 mL) and stirred for 1 hour at room temperature. The reaction mixture was concentrated in vacuo. The residue was dissolved in dichloromethane (25 mL) and a solution of benzylsulfonylchloride (2.25 g) in dichloromethane (10 mL) was added slowly at 0° C. Triethylamine was added to keep the pH at 8 during the reaction. The mixture was stirred for 1 hour at room temperature, whereafter the mixture was concentrated in vacuo. The residue was dissolved in ethyl acetate and washed with 5% sodium hydrogencarbonate solution, water and brine, dried over sodium sulfate, filtered and evaporated in vacuo. The residue was purified by chromatography on silica gel (eluent: dichloromethane/ethyl acetate 95/5 v/v) to yield BzlSO$_2$-norLeu(cyclo)-Gly-OMe (3.9 g).

TLC: Rf=0.40, dichloromethane/ethyl acetate 9/1 v/v on silica.

(j) BzlSO$_2$-norLeu(cyclo)-Gly-OH

A solution of BzlSO$_2$-norLeu(cyclo)-Gly-OMe (3.9 g) in dioxane/water 9/1 (100 mL) at room temperature was treated with sufficient 1N sodium hydroxide to keep the pH at 13 for 2 hours. After acidification, the mixture was poured into water and extracted with dichloromethane. The organic layer was washed with water and dried on sodium sulfate The filtrate was concentrated to yield 3.6 g of the title compound.

TLC: Rf 0.60, ethyl acetate/pyridine/acetic acid/water 63/20/6/11 v/v/v/v on silica.

(k) BzlSO$_2$-norLeu(cyclo)-Gly-Lys(Boc)Ψ[CHOHCO]-NHBzl

To a cold (0° C.) solution of BzlSO$_2$-norLeu(cyclo)-Gly-OH (340 mg) in N,N-dimethylformamide (10 mL) were successively added 1-hydroxybenzotriazole (HOBt, 203 mg) and dicyclohexylcarbodiimide (DCC, 217 mg). After stiring for 30 minutes at 0° C. H-Lys(Boc)Ψ[CHOHCO]-NHBzl.HCl (402 mg), prepared as described under (f), and triethylamine (0.15 mL) were added. The mixture was stirred at 0° C. for 1 hour and then kept at room temperature overnight. The mixture was cooled to −20° C. and dicyclohexylurea was removed by filtration. The filtrate was evaporated to dryness. The residue was dissolved in ethyl acetate and washed successively with 1M hydrochloric acid, water, aqueous 5% sodium hydrogencarbonate, water and brine, dried over sodium sulfate and concentrated in vacuo to afford BzlSO$_2$-norLeu(cyclo)-Gly-Lys(Boc)Ψ[CHOHCO]-NHBzl (690 mg).

TLC: Rf=0.75, ethyl acetate/pyridine/acetic acid/water= ll63/20/6/11 v/v/v/v on silica.

(l) BzlSO$_2$-norLeu(cyclo)-Gly-Lys(Boc)Ψ[COCO]-NHBzl

To a solution of BzlSO$_2$-norLeu(cyclo)-Gly-Lys(Boc)Ψ[CHOHCO]-NHBzl (680 mg) in dry dichloromethane (20 mL) was added 424 mg of periodinane (Dess-Martin reagent). After stirring at room temperature for one hour, aqueous 2% sodium thiosulfate solution (20 mL) and aqueous 5% sodium hydrogencarbonate solution (20 mL) were added and the mixture was stirred for 30 min at room temperature. The organic layer was separated, washed with water, dried over sodium sulfate, filtered and evaporated in vacuo to give crude BzlSO$_2$-norLeu(cyclo)-Gly-Lys(Boc)Ψ[COCO]-NHBzl (561 mg).

TLC: Rf=0.85, ethyl acetate/pyridine/acetic acid/water= 163/20/6/11 v/v/v/v on silica.

(m) BzlSO$_7$-norLeu(cyclo)-Gly-LysΨ[COCO]-NHBzl

BzlSO$_2$-norLeu(cyclo)-Gly-Lys(Boc)Ψ[COCO]-NHBzl (560 mg, crude) was treated with trifluoroacetic acid (10 mL) and stirred for 1 hour at room temperature. The reaction mixture was concentrated in vacuo and the residue dissolved in water and directly charged onto a preparative HPLC DeltaPak RP-C$_{18}$ column, which was subsequently eluted using a gradient elution system of 20% A/80% B to 20% A/45% B/35% C over 45 min at a flow rate of 80 mL/min. Yield: 287 mg of BzlSO$_2$-norLeu(cyclo)-Gly-LysΨ[COCO]—OH.

Rt (LC): 23.8 min, 20% A/60% B/20%C to 20% A/80% C in 30 min.

EXAMPLE 2

EthylSO$_2$-D-Cha-Pro-LysΨ[COCO]—OH (a) Boc-D-Cha-Pro-OPac

To a solution of Boc-D-Cha-OH.H$_2$O (21.5 g) in N,N-dimethylformamide (143 mL) at 0° C. were added hydroxybenzotriazole (HOBt) (13.7 g) and dicyclohexylcarbodiimide (DCC) (15.7 g) and stirred at 0° C. for 30 minutes. H-Pro-OPac. TFA (20 g) was disolved in 50 mL of N,N-dimethylformamide, the pH was adjusted to 8 with triethylamine and this solution was added to the reaction mixture. This was allowed to continue for 16 hours during which the temperature was increased to room temperature. The mixture was filtered, concentrated in vacuo, dissolved in ethylacetate, washed with 1N hydrochloric acid, water, 5% sodium hydrogencarbonate solution and brine, dried over sodium sulfate, filtered and evaporated in vacuo. Yield 28 g.

TLC: Rf=0.5, dichloromethane/methanol 95/5 v/v on silica.

(b) EthylSO$_2$-D-Cha-Pro-OPac

Boc-D-Cha-Pro-OPac (3.8 g) was dissolved in TFA/dichloromethane 1/1 v/v (25 mL) and stirred for 30 minutes at room temperature. The reaction mixture was evaporated in vacuo. The crude amine was dissolved in dichloromethane (50 mL) and ethanesulfonyl chloride (0.8 mL) was added at −78° C. Triethylamine was added to keep the pH at 8 during the reaction. The mixture was stirred for 3 hours at 0° C., whereafter water (25 mL) was added. After an additional stirring for 30 minutes at room temperature, the reaction mixture was concentrated in vacuo. The residue was dissolved in diethyl ether and washed with 1N hydrochloric acid, water, 5% sodium hydrogencarbonate solution and brine, dried over sodium sulfate, filtered and evaporated in vacuo. Trituration of the crude material with methanol yielded ethylSO$_2$-D-Cha-Pro-OPac (3.0 g).

TLC: Rf=0.6, dichloromethane/methanol 95/5 v/v on silica.

(c) EthylSO$_2$-D-Cha-Pro-OH

To a solution of ethylSO$_2$-D-Cha-Pro-OPac (10 g) in tetrahydrofuran (250 mL) was added 1M solution of tetrabutylammonium fluoride in tetrahydrofuran (84 mL). The reaction mixture was stirred for 30 minutes at room temperature and poured into water (1 L). The aqueous solution was extracted with ethyl acetate. The combined organic layers were successively washed with 1N hydrochloric acid and water, dried over sodium sulfate and concentrated in vacuo. The residue was purified by crystallisation from ethyl acetate/diisopropylether to yield EthylSO$_2$-D-Cha-Pro-OH (6.0 g).

TLC: Rf=0.2, ethyl acetate/pyridine/acetic acid/water 163/20/6/11 v/v/v/v on silica.

(d) EthylSO$_2$-D-Cha-Pro-LysΨ[COCO]—OH

The DCC/HOBt-coupling between EthylSO$_2$-D-Cha-Pro-OH and H-Lys(Boc)Ψ[CHOHCO]-OMe.HCl, saponification, Dess-Martin oxidation, deprotection and purification were done according to the procedures described in example 1. Yield: 163 mg of the title compound.

Rt (LC): 36.35 min. 20% A/80% B to 20% A/20% B/60% C in 40 min.

EXAMPLE 3

BzlSO$_2$-norLeu(cyclo)-Gly-LysΨ[COCO]-OEt

(a) Cbz-Lys(Boc) Ψ[CHOHCO]-OEt

Cbz-Lys(Boc) Ψ[CHOHCO]-OMe (751 mg) was dissolved in 25 mL of 3N HCl/ethanol solution and stirred during 4.5 hours at room temperature. The reaction solution was evaporated to dryness and coevaporated three times with ethanol to yield 691 mg of Cbz-Lys Ψ[CHOHCO]-OEt. This product was dissolved in 10 mL dry dichloromethane and di-tert-butyl dicarbonate (425 mg) was added. The pH of the solution was adjusted and maintained at 8 with triethylamine and the reaction was stirred for 16 hours at room temperature. Water was added and the organic layer was washed and dried to yield 782 mg of the desired product. After purification on silica using heptane/ethyl acetate 2/3 the final yield was 696 mg.

TLC: Rf 0.95, ethyl acetate/pyridine/acetic acid/water 232/31/18/7 v/v/v/v on silica.

(b) H-Lys(Boc)Ψ[CHOHCO]-OEt.HCl

To a solution of Cbz-Lys(Boc)Ψ[CHOHCO]-OEt (696 mg) in ethanol (25 mL) were added 10% palladium on activated carbon (100 mg) and 2N hydrochloric acid (0.8 mL) and this suspension was hydrogenated at atmospheric pressure for 50 minutes at room temperature. The palladium catalyst was removed by filtration and the filtrate was concentrated in vacuo to yield H-Lys(Boc)Ψ[CHOHCO]-OEt.HCl (525 mg).

TLC: Rf=0.17, ethyl acetate/pyridine/acetic acid/water= 232/31/18/7 v/v/v/v on silica.

(c) BzlSO$_2$-norLeu(cyclo)-Gly-LysΨ[COCO]-OEt

Coupling with BzlSO$_2$-norLeu(cyclo)-Gly-OH, oxidation, deprotection and purification were done according to procedures described in Example 1. Yield: 186 mg of the title compound.

Rt (LC): 32.46 min. 20% A/80% B to 20% A/20% B/60% C in 40 min.

EXAMPLE 4

BzlSO$_2$-norLeu(cyclo)-Gly-LysΨ[COCO]—NH$_2$

The coupling between BzlSO$_2$-norLeu(cyclo)-Gly-OH and H-Lys(Boc)Ψ[CHOHCO]—NH$_2$.HCl. and the subsequent oxidation, deprotection and purification were done according to procedures described in Example 1 to yield 103 mg of the title compound.

Rt (LC): 27.50 min. 20% A/80% B to 20% A/20% B/60% C in 40 min.

EXAMPLE 5

EthylSO$_2$-D-Cha-Pro-LysTr[COCO]-OEt

The DCC/HOBt-coupling between EthylSO$_2$-D-Cha-Pro-OH (270 mg) and H-Lys(Boc)Ψ[CHOHCO]-OEt.HCl (268 mg), Dess-Martin oxidation, deprotection using trifluoroacetic acid and purification were done according to the procedures described in Example 1. Yield: 41 mg of the title compound.

Rt (LC): 40.7 min. 20% A/80% B to 20% A/20% B/60% C in 40 min. and maintain this mixture of eluens for an additional 10 min.

EXAMPLE 6

EthylSO$_2$-D-Cha-Pro-LysΨ[COCO]-NHBzl

The DCC/HOBt-coupling between EthylSO$_2$-D-Cha-Pro-OH (250 mg) and H-Lys(Boc)Ψ[CHOHCO]-NHBzl.HCl (611 mg), Dess-Martin oxidation, deprotection using trifluoroacetic acid and purification were done according to the procedures described in Example 1. Yield: 208 mg of the title compound.

Rt (LC): 28.7 min. 20% A/60% B/20%C to 20% A/80% C in 30 min.

EXAMPLE 7

EthylSO$_2$-D-Cha-Pro-LysΨ[COCO]—NH$_2$

The procedures described in Example 1 were used to prepare the title compound. H-Lys(Boc)Ψ[CHOHCO]—

NH$_2$.HCl (0.84 g) was prepared from Cbz-Lys(Boc)Ψ[CHOHCO]—OH (0.95 g) as described for H-Lys(Boc)Ψ[CHOHCO]-NHBzl.HCl. Then DCC/HOBt-coupling between EthylSO$_2$-D-Cha-Pro-OH (189 mg) and H-Lys(Boc)Ψ[CHOHCO]—NH$_2$.HCl (179 mg), Dess-Martin oxidation, deprotection using trifluoroacetic acid and purification yielded 126 mg of the title compound.

Rt (LC): 36.3 min. 20% A/80% B to 20% A/20% B/60% C in 40 min.

EXAMPLE 8

BzlSO$_2$-norVal(cyclo)-Gly-LysΨ[COCO]—OH

(a) (S)-3-((benzyloxycarbonyl)amino)-2-oxo-piperidine

Cbz-Ornithine-OH.HCl (25 g) was dissolved in 2 L of N,N-dimethyl formamide and 12 mL of triethyl amine was added to a pH of 8.5. 2-(1H-benzotriazol-1-yl)-1,1,3,3-tetramethyluronium tetrafluoroborate (TBTU, 26.5 g) in 250 mL of N,N-dimethyl formamide was added dropwise under vigorous stirring. The mixture was allowed to react for 16 hours at room temperature while continously adjusting the pH with triethyl amine to 8.5. The reaction mixture was concentrated to dryness, dissolved in ethyl acetate and washed with 1N hydrochloric acid, water, 5% sodium hydrogen carbonate, water and brine, dried on sodium sulfate, filtered and evaporated to dryness to yield 11.7 g of the title compound.

TLC: Rf=0.80, ethyl acetate/pyridine/acetic acid/water= 63/20/6/11 v/v/v/v on silica.

(b) Cbz-norVal(cyclo)-Gly-OMe (S)-3-((benzyloxycarbonyl)amino)-2-oxo-piperidine (5 g) was dissolved in dichloromethane (50 mL). At −20° C. a 1M solution of lithium bis(trimethylsilyl)amide in tetrahydrofuran/cyclohexane 1/1 v/v (20 mL, 1 equiv.) was added slowly and the mixture was stirred for 30 min. Methyl bromoacetate (1.9 mL) was subsequently added and the mixture was stirred for 30 minutes at room temperature. The mixture was diluted with ethyl acetate and quenched with a saturated aquous ammonium chloride solution. The organic layer was washed with water and brine, dried over sodium sulfate, filtered and evaporated in vacuo. The residue was purified by chromatography on silica gel (eluent: dichloromethane/methanol 95/5 v/v) to yield 4.7 g Cbz-norVal(cyclo)-Gly-OMe.

TLC: Rf=0.38,ethyl acetate/heptane 3/1 v/v on silica.

(c) BzlSO$_2$-norVal(cyclo)-Gly-OMe

Cbz-norVal(cyclo)-Gly-OMe (4.7 g) was dissolved in 40 mL of methanol, 500 mg 10% palladium on charcoal was added, 7.4 mL of a 2N hydrochloric acid was added and hydrogenated at atmospheric pressure for 1 hour at room temperature. The reaction mixture was filtered, evaporated in vacuo and immediately used in the next step as H-norVal(cyclo)-Gly-OMe.HCl.

The crude amine was dissolved in dichloromethane (50 mL) and benzylsulfonylchloride (2.82 g) was added slowly at 0° C. Triethylamine was added to keep the pH at 8 during the reaction. The mixture was stirred for 1 hour at room temperature, whereafter the mixture was washed with water and brine, dried over sodium sulfate, filtered and evaporated in vacuo. The residue was purified by chromatography on silica gel (eluent: dichloromethane/methanol 95/5 v/v) to yield BzlSO$_2$-norVal(cyclo)-Gly-OMe (2 g).

TLC: Rf=0.87, ethyl acetate/pyridine/acetic acid/water= 63/20/6/11 v/v/v/v on silica.

(d) BzlSO$_2$-norVal(cyclo)-Gly-OH

The saponification of BzlSO$_2$-norVal(cyclo)-Gly-OMe (2 g) was done according to the procedure described in Example 1. Yield: 1.8 g.

TLC: Rf=0.40, ethyl acetate/pyridine/acetic acid/water= 63/20/6/11 v/v/v/v on silica.

(e) BzlSO$_2$-norVal(cyclo)-Gly-LysΨ[COCO]—OH

Coupling between BzlSO$_2$-norVal(cyclo)-Gly-OH and H-Lys(Boc)Ψ[CHOHCO]-OMe.HCl, saponification, oxidation, deprotection and purification were done according to procedures described in Example 1. Yield: 107 mg of the title compound.

Rt (LC): 24.45 min. 20% A/80% B to 20% A/20% B/60% C in 40 min.

EXAMPLE 9

EthylSO-D-Cha-Pro-LysΨ[COCO]-O-iPropyl

H-Lys(Boc)Ψ[CHOHCO]—O-i-Propyl.HCl (0.32 g) was prepared using the procedure described for H-Lys(Boc)Ψ[CHOHCO]-OEt.HCl in Example 3 starting from Cbz-Lys(Boc)Ψ[CHOHCO]-OMe (0.49 g) and 2-propanol. The DCC/HOBt-coupling between EthylSO$_2$-D-Cha-Pro-OH (239mg) and H-Lys(Boc)Ψ[CHOHCO]—O-i-Propyl.HCl (316 mg), Dess-Martin oxidation, deprotection using trifluoroacetic acid and purification were done according to the procedures described in Example 1. Yield: 123 mg of the title compound.

Rt (LC): 43.0 min. 20% A/80% B to 20% A/20% B/60% C in 40 min. and maintain this mixture of eluens for an additional 10 min.

EXAMPLE 10

BzlSO$_2$-norVal(cyclo)-Gly-LysΨ[COCO]-Azetidine

The procedures described in Example 1 were used to prepare the title compound. Cbz-Lys(Boc)Ψ[CHOHCO]-Azetidine (2.26 g) was prepared from Cbz-Lys(Boc)Ψ[CHOHCO]—OH (2.7 g) as described for Cbz-Lys(Boc)Ψ[CHOHCO]-NHBzl. Hydrogenation of Cbz-Lys(Boc)Ψ[CHOHCO]-Azetidine (269 mg) yielded H-Lys(Boc)Ψ[CHOHCO]-Azetidine.HCl (214 mg). Then DCC/HOBt-coupling between BzlSO$_2$-norVal(cyclo)-Gly-OH (175 mg) and H-Lys(Boc)Ψ[CHOHCO]-Azetidine.HCl (214 mg), Dess-Martin oxidation, deprotection using trifluoroacetic acid and purification yielded 84 mg of the title compound.

Rt (LC): 27.8 min. 20% A/80% B to 20% A/20% B/60% C in 40 min.

EXAMPLE 11

BzlSO$_2$-norLeu(cyclo)-Gly-LysΨ[COCO]-Azetidine

Cbz-Lys(Boc)Ψ[CHOHCO]-Azetidine was prepared according to procedures described in Example 10. The hydrogenation, coupling to BzlSO$_2$-norLeu(cyclo)-Gly-OH, oxidation, deprotection and purification were also done according to procedures described in Example 1. Yield: 100 mg of the title compound.

Rt (LC): 33.61 min. 20% A/80% B to 20% A/20% B/60% C in 40 min.

EXAMPLE 12

BzlSO$_2$-norLeu(cyclo)-Gly-Lys(Ethoxycarbonyl)Ψ[COCO]-Azetidine (a) BzlSO$_2$-norLeu(cyclo)-Gly-LysΨ[CHOHCO]-Azetidine.TFA BzlSO$_2$-norLeu(cyclo)-Gly-Lys(Boc)Ψ[CHOHCO]-Azetidine (prepared according to procedures described in Example 10) (220 mg) was dissolved in 10 mL of dichloromethane/trifluoroacetic acid 1/1 v/v and stirred for 2 hours at room temperature. Solvents were removed by evaporation and the residue titruated with diethyl ether. Yield: 267 mg.

TLC: Rf=0.57, ethyl acetate/pyridine/acetic acid/water=63/20/6/11 v/v/v/v on silica.

(b) BzlSO$_2$-norLeu(cyclo)-Gly-Lys(Ethoxycarbonyl)Ψ[CHOHCO]-Azetidine

BzlSO$_2$-norLeu(cyclo)-Gly-LysΨ[CHOHCO]-Azetidine.TFA (267 mg) was dissolved in 10 mL of N,N-dimethylformamide and 46 μL of ethylchloroformate was added after which the pH was adjusted to 8.5 with triethylamine. After stirring for 16 hours at room temperature, the reaction mixture was diluted with ethyl acetate, washed with water, 5% sodium hydrogencarbonate, 2% citric acid and brine, dried on sodium sulfate, filtered and evaporated to dryness to yield 150 mg of the title compound.

TLC: Rf=0.53, dichloromethane/methanol 9/1 v/v on silica.

(c) BzlSO$_2$-norLeu(cyclo)-Gly-Lys(Ethoxycarbonyl)Ψ[COCO]-Azetidine

Oxidation and purification of BzlSO$_2$-norLeu(cyclo)-Lys(Ethoxycarbonyl)Ψ[CHOHCO]-Azetidine (150 mg) were done according to procedures described in Example 1. Yield 25 mg.

Rt (LC): 26.42 min. 20% A/60% B/20%C to 100% C in 40 min.

EXAMPLE 13

BzlSO$_2$-norLeu(cyclo)-Gly-LysΨ[COCO]—O-iPropyl

Coupling between BzlSO$_2$-norLeu(cyclo)-Gly-OH (described in Example 1) and H-Lys(Boc)Ψ[CHOHCO]—O-iPropyl.HCl (described in Example 9), oxidation, deprotection and purification were done according to procedures described in Example 1. Yield: 400 mg of the title compound.

Rt (LC): 40 min. 20% A/80% B to 20% A/20% B/60% C in 40 min.

EXAMPLE 14

BzlSO?-norLeu(cyclo)-Gly-LysΨ[COCO]—NH-iPropyl (a) BzlSO?-norLeu(cyclo)-Gly-Lys(Boc)Ψ[CHOHCO]—OH The DCC/HOBt-coupling between 1.96 g of BzlSO$_2$-norLeu(cyclo)-Gly-OH and 2.20 g of H-Lys(Boc)Ψ[CHOHCO]-OMe.HCl and saponification of the product were performed according to the procedures described in example 1. Yield: 3.1 g of the crude title compound.

TLC: Rf=0.4, ethyl acetate/pyridine/acetic acid/water=66/20/6/11 v/v/v/v on silica.

(b) BzlSO$_2$-norLeu(cyclo)-Gly-Lys(Boc)Ψ[CHOHCO]—NH-iPropyl

The EDCI/HOBt-coupling between 0.4 mmol BzlSO$_2$-norLeu(cyclo)-Gly-Lys(Boc)Ψ[CHOHCO]—OH and 0.105 mL of isopropylamine, Dess Martin oxidation (reaction time: 19 h) and deprotection were done according to the procedures described in example 1. Yield: 150 mg of the title compound.

Rt(LC): 34.01 min. 20% A/80% B to 20% A/20% B/60% C in 40 min.

EXAMPLE 15

BzlSO$_2$-norLeu(cyclo)-Gly-LysΨ[COCO]—NH-nPropyl

The EDCI/HOBt-coupling between 0.4 mmol BzlSO$_2$-norLeu(cyclo)-Gly-Lys(Boc)TΨ[CHOHCO]—OH and 0.101 mL of propylamine, Dess Martin oxidation (reaction time: 24 h) and deprotection were done according to the procedures described in example 1. Yield: 144 mg of the title compound.

Rt(LC): 34.22 min. 20% A/80% B to 20% A/20% B/60% C in 40 min.

EXAMPLE 16

BzlSO$_2$-norLeu(cyclo)-Gly-LysΨ[COCO]—NH-Methyl

The EDCI/HOBt-coupling between 0.4 mmol BzlSO$_2$-norLeu(cyclo)-Gly-Lys(Boc)Ψ[CHOHCO]—OH and methylamine (0.4 mL of a 3 M solution in N,N-dimethylformamide), Dess Martin oxidation (reaction time: 20 h) and deprotection were done according to the procedures described in example 1. Yield: 127 mg of the title compound.

Rt(LC): 28.36 min. 20% A/80% B to 20% A/20% BI 60% C in 40 min.

EXAMPLE 17

BzlSO$_2$-norLeu(cyclo)-Gly-LysΨ[COCO]-pyrrolidinyl

The EDCI/HOBt-coupling between 0.4 mmol BzlSO$_2$-norLeu(cyclo)-Gly-Lys(Boc)Ψ[CHOHCO]—OH and 0.102 mL of pyrrolidine, Dess Martin oxidation (reaction time: 14 days) and deprotection were done according to the procedures described in example 1. Yield: 125 mg of the title compound.

Rt(LC): 36.87 and 37.38 min. 20% A/80% B to 20% A/20% B/60% C in 40 min.

EXAMPLE 18

BzlSO$_2$-norLeu(cyclo)-Gly-LysyΨ[COCO]-N-Ethyl

The EDCI/HOBt-coupling between 0.4 mmol BzlSO$_2$-norLeu(cyclo)-Gly-Lys(Boc)Ψ[CHOHCO]—OH and ethylamine (1.78 mL of a 0.7 M solution in N,N-dimethylformamide), Dess Martin oxidation (reaction time: 20 h) and deprotection were done according to the procedures described in example 1. Yield: 115 mg of the title compound.

Rt(LC): 31.30 min. 20% A/80% B to 20% A/20% B/60% C in 40 min.

EXAMPLE 19

BzlSO$_2$-norLeu(cyclo)-Gly-LysΨ[COCO]-morpholin-4-yl

The EDCI/HOBt-coupling between 0.4 mmol BzlSO$_2$-norLeu(cyclo)-Gly-Lys(Boc)Ψ[CHOHCO]—OH and 0.107 mL of morpholine, Dess Martin oxidation (reaction time: 6.5 days) and deprotection were done according to the procedures described in example 1. Yield: 148 mg of the title compound.

Rt(LC): 33.73 and 34.17 min. 20% A/80% B to 20% A/20% B/60% C in 40 min.

EXAMPLE 20

BzlSO$_2$-norLeu(cyclo)-Gly-LysΨ[COCO]-(1,1-dioxo)thiomorpholin4-yl

To a solution of 2.47 g of thiomorpholine in 25 mL of methanol was added 5.75 g of di-tert-butyl dicarbonate and 4 mL of triethylamine. After stirring at room temperature for 3h, 50 mL of ethyl acetate was added and this solution was washed with water adjusted to pH 3 with hydrochloric acid, water, aqueous 5% sodium hydrogencarbonate and brine, dried over magnesium sulfate and concentrated to give 4.73 g of N-tert-butyloxycarbonyl thiomorpholine. This residue (4.73 g) was dissolved in 50 mL of dichloromethane and 50 mL of water was added. To this stirred mixture was added 11 g 3-chloroperoxybenzoic acid (80–90% purity) in small portions keeping the reaction mixture at pH 7. After stirring at room temperature for 16 h the water layer was separated, the organic layer washed with 5% aqueous sodium thiosulfate, 5% aqueous sodium hydrogencarbonate (three times) and brine, dried over magnesium sulfate and concentrated. The residue was purified by chromatography on silica gel (eluent: ethyl acetate/heptanes 2/3 v/v) to give 5.7 g of N-tert-butyloxycarbonyl thiomorpholine 1,1-dioxide. This sulfon (0.625 g) was dissolved in 50 mL of a 3M hydrogenchloride solution in dioxane and after stirring for 4 hours at room temperature the reaction mixture was concentrated to give 0.579 g of thiomorpholine 1,1-dioxide hydrochloride.

The EDCI/HOBt-coupling between 0.4 mmol BzlSO$_2$-norLeu(cyclo)-Gly-Lys(Boc)Ψ[CHOHCO]—OH and 0.21 g of thiomorpholine 1,1-dioxide hydrochloride, Dess Martin oxidation (reaction time: 3 days) and deprotection were done according to the procedures described in example 1. Yield: 180 mg of the title compound.

Rt(LC): 33.64 min. 20% A/80% B to 20% A/20% B/60% C in 40 min.

EXAMPLE 21

BzlSO$_2$-norLeu(acico)-Gly-LysΨ[COCO]-N(Methyl)(Methoxy)

The EDCI/HOBt-coupling between 0.4 mmol BzlSO$_2$-norLeu(cyclo)-Gly-Lys(Bc)Ψ[CHOHCO]—OH and 0.12 g of N,O-dimethylhydroxylamine, Dess Martin oxidation (reaction time: 3.5 days) and deprotection were done according to the procedures described in example 1. Yield: 136 mg of the title compound.

Rt(LC): 33.80 and 34.53 min. 20% A/80% B to 20% A/20% Bt 60% C in 40 min.

EXAMPLE 22

BzlSO$_2$-norLeu(cyclo)-Gly-LysΨ[COCO]-(2-(carboxamid)azetidin-1-yl)

The DCC/HOBt-coupling between 1.13 g N-tert-butyloxycarbonyl-L-azetidine-2-carboxylic acid and 1.38 g ammmonium chloride was performed as described in example 1 to give 0.468 g of N-tert-butyloxycarbonyl-L-azetidine-2-carboxamide. This amide (0.224 g) was dissolved in 5 mL of a 3M hydrogenchloride solution in dioxane. After stirring for 3 hours at room temperature the reaction mixture was concentrated to give 0.17 g of azetidine-2-carboxamide hydrochloride.

The EDCI/HOBt-coupling between 0.4 mmol BzlSO$_2$-norLeu(cyclo)-Gly-Lys(Boc)Ψ[CHOHCO]—OH and 0.17 g of azetidine-2-carboxamide hydrochloride, Dess Martin oxidation (reaction time: 20 h) and deprotection were done according to the procedures described in example 1. Yield: 58 mg of the title compound.

Rt(LC): 26.43 min. 20% A/80% B to 20% A/20% B/60% C in 40 min.

EXAMPLE 23 nPropylSO$_2$-D-Cha-Pro-LysΨ[COCO]—O-iPropyl (a) Boc-D-Cha-Pro-OBzl

To a stirred solution of 11.64 g of Boc-D-Cha-OH in 100 mL of dichloromethane at 0° C. was added 6.36 g of HOBt and 9.72 g of DCC. After 20 minutes a solution of 10.35 g of H-Pro-OBzl.HCl in 40 mL of dichloromethane adjusted with N,N-diisopropyl ethylamine to pH 8 was added. After 16 h the reaction mixture was filtered and the filtrate was washed successively with water, 0.1 N hydrochloric acid, water, aqueous 5% sodium hydrogencarbonate and brine. All aqueous washes were extracted twice with ethyl acetate, all organic extracts combined, dried over sodium sulfate and concentrated. To the residue was added a mixture of ethyl acetate/heptanes=1/1 (v/v), the resulting suspension filtered and the filtrate purified by chromatography on silica gel (eluent: ethyl acetate/heptanes=1/1 v/v) to yield 19.34 g of Boc-D-Cha-Pro-OBzl.

TLC: Rf=0.8, dichloromethane/methanol=9/1 v/v on silica.

(b) nPropylSO$_2$-D-Cha-Pro-OBzl

Boc-D-Cha-Pro-OBzl (1.01 g) was dissolved in 42 mL of a 3M hydrogenchloride solution in dioxane. After stirring for 2 hours at room temperature the reaction mixture was concentrated. The residue was dissolved in 35 mL of dichloromethane and cooled to 0° C. To this stirred solution was added 0.22 mL of 1-propanesulfonyl chloride and the pH adjusted to 8.5. After stirring for 24 h at room temperature the reaction mixture was concentrated. The residue was dissolved in ethyl acetate, washed successively with aqueous 5% sodium hydrogencarbonate, water, aqueous 5% citric acid and brine, dried over magnesium sulfate and concentrated. The crude product was purified by chromatography on silica gel (eluent: ethyl acetate/heptanes=1/1 v/v) to yield 0.85 g of nPropylSO$_2$-D-Cha-Pro-OBzl.

TLC: Rf=0.6, ethyl acetate/heptanes=1/1 v/v on silica.

(c) nPropylSO$_2$-D-Cha-Pro-LysΨ[COCO]—O-iPropyl nPropylSO$_2$-D-Cha-Pro-OBzl (0.85 g) was hydrogenated using the procedure described in example 1 to give 0.54 g of nPropylSO$_2$-D-Cha-Pro-OH. The DCC/HOBt coupling of 225 mg of nPropylSO$_2$-D-Cha-Pro-OH and of H-Lys(Boc)Ψ[CHOHCO]—O-iPropyl.HCl and Dess Martin oxidation were performed according to the procedures described in example 9. The Boc-group was removed using a 3M hydrogenchloride solution in dioxane as described above and the crude product purified using the preparative HPLC method described in example 1. Yield: 47 mg of the title compound.

Rt(LC): 27.6 min. 20% A/60% B/20% C to 20% A/80% C in 30 min, then to 100% C in 10 min.

EXAMPLE 24

(10-Camphor)SO$_2$-D-Cha-Pro-LysΨ[COCO]—O-iPropyl

The title compound was prepared from Boc-D-Cha-Pro-OBzl and (−)-10-camphorsulfonyl chloride using the procedures described in example 23. Yield 12% from Boc-D-Cha-Pro-OBzl.

Rt(LC): 33.6 min. 20% A/60% B/20% C to 20% A/80% C in 30 min, then to 100% C in 10 min.

EXAMPLE 25

PhenylSO$_2$-D-Cha-Pro-LysΨ[COCO]—O-iPropyl

The title compound was prepared from Boc-D-Cha-Pro-OBzl and benzenesulfonyl chloride using the procedures described in example 23. Yield: 9% from Boc-D-Cha-Pro-OBzl.

Rt(LC): 29.3 min. 20% A/60% B/20% C to 20% A/80% C in 30 min, then to 100% C in 10 min.

EXAMPLE 26

Methyl SO$_2$-D-Cha-Pro-LysΨ[COCO]—O-iPropyl

The title compound was prepared from Boc-D-Cha-Pro-OBzl and methanesulfonyl chloride using the procedures described in example 23. Yield: 18% from Boc-D-Cha-Pro-OBzl.

Rt(LC): 24.3 min. 20% A/60% B/20% C to 20% A/80% C in 30 min, then to 100% C in 10 min.

EXAMPLE 27 iPropyl SO$_2$-D-Cha-Pro-LysΨ[COCO]—O-iPropyl

The title compound was prepared from Boc-D-Cha-Pro-OBzl and isopropylsulfonyl chloride using the procedures described in example 23. Yield: 2% from Boc-D-Cha-Pro-OBzl.

Rt(LC): 26.8 min. 20% A/60% B/20% C to 20% A/80% C in 30 min, then to 100% C in 10 min.

EXAMPLE 28

BenzylSO$_2$-D-Cha-Pro-LysΨ[COCO]—O-iPropyl

The title compound was prepared from Boc-D-Cha-Pro-OBzl and a-toluenesulfonyl chloride using the procedures described in example 23. Yield: 11% from Boc-D-Cha-Pro-OBzl.

Rt(LC): 30.4 min. 20% A/60% B/20% C to 20% A/80% C in 30 min, then to 100% C in 10 mi.

EXAMPLE 29 nButylSO$_2$-D-Cha-Pro-LysΨ[COCO]—O-iPropyl

The title compound was prepared from Boc-D-Cha-Pro-OBzl and 1-butanesulfonyl chloride using the procedures described in example 23. Yield: 29% from Boc-D-Cha-Pro-OBzl.

Rt(LC): 29.3 min. 20% A/60% B/20% C to 20% A/80% C in 30 min, then to 100% C in 10 min.

EXAMPLE 30

[3-(benzylsulfonylamino)-6-methyl-2-oxo-1,2-dihydropyridinyl]-acetyl-LysΨ[COCO]—O-iPropyl The DCC/HOBt coupling of 151 mg of [3-(benzylsulfonylamino)-6-methyl-2-oxo-1,2-dihydropyridinyl]-acetic acid (WO 97/01338) and 205 mg of H-Lys(Boc)Ψ[CHOHCO]—O-iPropyl.HCl, Dess Martin oxidation, deprotection and purification were performed according to the procedures described in example 9 to give 1 mg of the title compound.

Rt(LC): 34.7 min. 20% A/80% B to 20% A/20% B/60% C in 40 min.

EXAMPLE 31

[3-(benzylsulfonylamino)-2-oxo-1,2-dihydropyridinyl]-acetyl-LysΨ[COCO]—O-iPronyl The DCC/HOBt coupling of 178 mg of [3-(benzylsulfonylamin6)-2-oxo-1,2-dihydropyridinyl]-acetic acid (WO 97/46207) and H-Lys(Boc)Ψ[CHOHCO]—O-iPropyl.HCl and Dess Martin oxidation were performed according to the procedures described in example 9. Deprotection using hydrogenchloride in dioxane and purification were performed according to the procedures described in example 23 to give 116 mg of the title compound.

Rt(LC): 32.4 min. 20% A/80% B to 20% A/20% B/60% C in 40 min.

EXAMPLE 32

[3-(benzylsulfonylamino)-6-methyl-2-oxo-1,2-dihydropyridinyl]-acetyl-LysΨ[COCO]—NH$_2$ The DCC/HOBt coupling of 286 mg of [3-(benzylsulfonylamino)-6-methyl-2-oxo-1,2-dihydropyridinyl]-acetic acid (WO 97/01338) and H-Lys(Boc)Ψ[CHOHCO]-OMe HCl, according to the procedure described in example 1 yielded 0.51 g of [3-(benzylsulfonylamino)-6-methyl-2-oxo-1,2-dihydropyridinyl]-acetyl-LysΨ[CHOHCO]-OMe. Saponification of this methyl ester, EDCI/HOBt coupling with ammonium chloride, Dess Martin oxidation, deprotection and purification were performed according to the procedures described in example 14 to give 76 mg of the title compound.

Rt(LC): 26.9 min. 20% A/80% B to 20% A/20% B/60% C in 40 min.

EXAMPLE 33

BzlSO$_2$-Aad-Pro-LysΨ[COCO]—OH (a) BzlSO$_2$-Aad(OtBu)-OH

To a stirred solution of 0.5 g of H-Aad(OtBu)-OH in 4.4 mL of aqueous 1 N sodium hydroxide was added 0.42 g of benzylsulfonylchloride in 2 mL of dioxane. After 16 hours at room temperature, additional 1.4 mL of aqueous 2 N sodium hydroxide, 0.5 mL of dioxane and 0.09 g of benzylsulfonylchloride were added and the reaction mixture stirred for an additional day. The dioxane was removed, water was added, the mixture made acid (pH 3) using hydrochloric acid and extracted twice with diethyl ether. The combined ether layers were dried over sodium sulfate and concentrated to give 235 mg of BzlSO$_2$-Aad(OtBu)-OH.

TLC: Rf=0.7, dichloromethane/methanol/water=14/6/1 v/v/v on silica.

(b) BzlSO$_2$-Aad(OtBu)-Pro-OH

DCC/HOBt coupling of 235 mg of BzlSO$_2$-Aad (OtBu)-OH and 168 mg of H-Pro-OBzl.HCl followed by hydrogenation as described in example 23 yielded 193 mg of the title compound.

TLC: Rf=0.6, ethyl acetate/pyridine/acetic acid/water#163/20/6/11 v/v/v/v on silica.

(c) BzlSO$_2$-Aad-Pro-LysΨ[COCO]—OH

The DCC/HOBt coupling of 193 mg of BzlSO$_2$-Aad (OtBu)-Pro-OH and H-Lys(Boc)Ψ[CHOHCO]-OMe HCl, saponification, Dess Martin oxidation, deprotection and purification were performed according to the procedures described in example 32 to give 85 mg of the title compound.

Rt(LC): 26.1 min. 20% A/80% B to 20% A/20% B/60% C in 40 min.

EXAMPLE 34

BzlSO$_2$-Glu-Pro-LysΨ[COCO]—OH

Starting with H-Glu(OtBu)-OH according to the route described in example 33 gave the title compound. Yield: 3% from H-Glu(OtBu)-OH.

Rt(LC): 22.6 min. 20% A/80% B to 20% A/20% B/60% C in 40 min.

EXAMPLE 35

BzlSO$_2$-Asp-Pro-LysΨ[COCO]—OH

Starting with H-Asp(OtBu)-OH according to the route described in example 33 gave the title compound. Yield: 18% from H-Asp(OtBu)-OH.

Rt(LC): 21.9 min. 20% A/80% B to 20% A/20% B/60% C in 40 min.

EXAMPLE 36

EtSO$_2$-D-Tyr(Me)-Pro -LysΨ[COCO]—NH (a) EtSO-D-Tyr(Me)-Pro-OH

DCC/HOBt coupling of 2.22 g of Boc-D-Tyr(Me)-OH and 2.0 g of H-Pro-OBzl.HCl, removal of the Boc protecting group, sulfonylation using ethane sulfonyl chloride and hydrogenation of the benzyl ester using the procedures described in example 23 yielded 1.0 g of the title compound.

TLC: Rf=0.23, dichloromethane/methanol=95/5 v/v on silica.

(b) EtSO$_2$-D-Tyr(Me)-Pro -LysΨ[COCO]—NH$_2$

The DCC/HOBt coupling of 254 mg of EtSO$_2$-D-Tyr (Me)-Pro-OH and H-Lys(Boc)Ψ[CHOHCO]-OMe.HCl, saponification, EDCI/HOBt coupling with ammonium chloride, Dess Martin oxidation, deprotection and purification were performed according to the procedures described in example 32 to give 83 mg of the title compound.

Rt(LC): 28.0 min. 20% A/80% B to 20% A/20% B/60% C in 40 min.

EXAMPLE 37

EtSO$_2$-D-Tyr(Me)-Pro -LysΨ[COCO]—O-iPropyl

The DCC/HOBt coupling of 0.51 g of EtSO$_2$-D-Tyr(Me)-Pro-OH and H-Lys(Boc)Ψ[CHOHCO]—O-iPropyl.HCl, Dess Martin oxidation, deprotection and purification were performed according to the procedures described in example 9 to give 223 mg of the title.

Rt(LC): 36.5 min. 20% A/80% B to 20% A/20% B/60% C in 40 min.

EXAMPLE 38

EtSO$_2$-D-Tyr(Me)-Pro -LysΨ[COCO]-Azetidine

The DCC/HOBt coupling of 307 mg of EtSO$_2$-D-Tyr (Me)-Pro-OH and H-Lys(Boc)Ψ[CHOHCO]-Azetidine.HCl, Dess Martin oxidation, deprotection and purification were performed according to the procedures described in example 10 to give 83 mg of the title compound.

Rt(LC): 36.4 min. 20% A/80% B to 20% A/20% B/60% C in 40 min.

EXAMPLE 39

EtSO$_2$-D-Tyr(Me)-Pro -LysΨ[COCO]-N-(4-chloropropyl)

The title compound (43 mg) was obtained as second product in the purification of example 38.

Rt(LC); 38.1 min. 20% A/80% B to 20% A/20% B/60% C in 40 min.

EXAMPLE 40

BzlSO$_2$-D-Dpa-Pro-LysΨ[COCO]—O-iPropyl (a) BzlSO$_2$-D-Dpa-Pro-OH

Removal of the Boc group of 1.5 g of Boc-D-Dpa-Pro-OBzl (WO 97/31937), reaction with benzylsulfonyl chloride and removal of the benzyl ester according to the procedures described in example 23 to yield 1.0 g of the title compound.

TLC: Rf=0.63, ethyl acetate/pyridine/acetic acid/water= 163/20/6/11 v/v/v/v on silica.

(b) BzlSO$_2$-D-Dpa-Pro-LysΨ[COCO]—O-iPropyl

The DCC/HOBt coupling of 0.31 g of BzlSO$_2$-D-Dpa-Pro-OH and H-Lys(Boc)Ψ[CHOHCO]-O-iPropyl.HCl, Dess Martin oxidation, deprotection and purification were performed according to the procedures described in example 9 to give 50 mg of the title compound.

Rt(LC): 32.2 min. 20% A/60% B/20%C to 20% A/80% C in 30 min, then to 100% C in 10 min.

EXAMPLE 41

EtSO$_2$-Leu-Pro-LysΨ[COCO]—O-iPropyl (a) EtSO$_2$-Leu-OMe

A stirred solution of 3.0 g of H-Leu-OMe.HCl in 30 mL of dichloromethane was adjusted to pH 8 using triethylamine and cooled at 0° C. Then 3.2 mL of ethanesulfonyl chloride and 2.3 mL of triethylamine were added. After stirring for 16 h at room temperature the reaction mixture was washed successively with 0.5 N hydrochloric acid, water and aqueous 5% sodium hydrogencarbonate and concentrated. The crude product was purified by chromatography on silica gel (eluent: dichloromethane/methanol=9/1 v/v) to yield 3.3 g of EtSO$_2$-Leu-OMe.

TLC: Rf=0.69, dichloromethane/ethyl acetate=9/1 v/v on silica.

(b) EtSO$_2$-Leu-Pro-OH

EtSO$_2$-Leu-OMe (3.3 g) was saponified (procedure example 1), coupled with H-Pro-OBzl (procedure example 23) and the resulting dipeptide was hydrogenated (procedure example 23) using the indicated procedures to give 3.4 g of the title compound.

TLC: Rf=0.11, dichloromethane/ethyl acetate=9/1 v/v on silica.

(c) EtSO$_2$-Leu-Pro-LysΨ[COCO]—O-iPropyl

The DCC/HOBt coupling of 145 mg of EtSO$_2$-Leu-Pro-OH and H-Lys(Boc)Ψ[CHOHCO]—O-iPropyl.HCl, Dess Martin oxidation, deprotection and purification were performed according to the procedures described in example 23 to give 120 mg of the title compound.

Rt(LC): 16.6 min. 20% A/60% B/20%C to 20% A/80% C in 30 min.

EXAMPLE 42

BzlSO$_2$-norLeu(cyclo)-Gly-Acp Ψ[COCO]-Azetidine (a) H-Acg(Boc)[CHOHCO]-OMe.HCl To a solution of 3-[4-(1,1-dimethylethoxycarbonylamino)cyclohexyl]-2-hydroxy-3-nitro-propionic acid methyl ester (Lyle et al, Bioorg. Med. Chem. Lett., 7, 67–72 (1997)) (294 mg) in methanol (100 mL) was added 2N hydrochloric acid (0.425 mL) and 10% palladium on activated carbon powder (0.45 g) and this suspension was hydrogenated at atmospheric pressure at room temperature for 16 hours. The palladium catalyst was removed by filtration and the solvent was removed by evaporation at reduced pressure yielding H-Acg(Boc)Ψ[CHOHCO]-OMe.HCl (289 mg) as a mixture of diastereomers.

TLC: Rf=0.26, silica gel, ethyl acetate/pyridine/acetic acid/water=232/31/18/7 v/v/v/v.

(b) BzlSO$_2$-norLeu(cyclo)-Gly-AcgΨ[COCO]-Azetidine

The DCC/HOBt-coupling between 0.27 g of BzlSO$_2$-norLeu(cyclo)-Gly-OH and 0.25 g of H-Acg(Boc)Ψ[CHOHCO]-OMe.HCl, saponification, EDCI/HOBt-coupling with azetidine hydrochloride, Dess Martin oxidation and deprotection were done according to the procedures described in example 1. Yield: 82 mg of the title compound.

Rt(LC): 34.8 and 35.4 min. 20% A/80% B to 20% A/20% B/60% C in 40 min.

EXAMPLE 43

EthylSO$_2$-D-Cha-Pro-AcgΨ[COCO]-OiPropyl (a) Cbz-Acg(aoc)Ψ[CHOHCO]-OMe

A stirred solution of 0.34 g of H-Acg(Boc)Ψ[CHOHCO]-OMe.HCl in 10 mL of acetonitrile and 10 mL of N,N-dimethylformamide is adjusted to pH 8 using N,N-diisopropylethylamine. To this solution 0.24 g of N-benzyloxycarbonyloxysuccinimide was added. After stirring at room temeperature for one hour the reaction mixture was concentrated. The residue dissolved in ethyl acetate, washed with water and brine, dried over sodium sulfate and concentrated. The residue was purified by chromatography on silica gel (eluent: ethyl acetate/heptanes 2/3 v/v) to give 0.287 mg of Cbz-Acg(Boc)Ψ[CHOHCO]-OMe.

TLC: Rf=0.25, ethyl acetate/heptanes 1/1 v/v on silica.

(b) Cbz-Acg(Boc)ΨΨ[CHOHCO]-OiPropyl

To a stirred mixture of 5 mL of tetrahydrofuran and 1 mL of 2-propanol under a nitrogen atmosphere was added slowly added 2.5 mL of a 1.6N n-butyllithium solution in hexanes. After 20 minutes a solution of 0.28 g of Cbz-Acg(Boc)Ψ[CHOHCO]-OMe in 5 mL of 2-propanol was added and stirred for 2 h at room temperature. Then 0.5 mL of acetic acid was added and the reaction mixture was concentrated. The residue dissolved in ethyl acetate, washed with water, dried over sodium sulfate and concentrated. The residue was purified by chromatography on silica gel (eluent: ethyl acetate/heptanes 2/3 v/v) to give 0.223 mg of Cbz-Acg(Boc)ΨΨ[CHOHCO]-OiPropyl.

TLC: Rf=0.25, ethyl acetate/heptanes 1/2 v/v on silica.

(b) EthylSO$_2$-D-Cha-Pro-AcgΨ[COCO]-OiPropyl

To a solution of 0.22 g of Cbz-Acg(Boc)Ψ[CHOHCO]-OiPropyl in N,N-dimethylformamide were added 10% palladium on activated carbon (80 mg) and 2M hydrochloric acid (0.23 mL) and this suspension was hydrogenated at atmospheric pressure for 1 hour at room temperature. The palladium catalyst was removed by filtration. This fitrate was used in a DCC/HOBt coupling with 0.166 g of EthylSO$_2$-D-Cha-Pro-OH using the procedure described in example 1. The product was oxidised using the Dess Martin reagent, the Boc-group removed and purified using the procedures described in example 1. Yield: 100 mg of the title compound.

Rt(LC): 30.0 min. 20% A/60% B/20% C to 20% A/80% C in 30 min

EXAMPLE 44

Preparation of EtSO$_2$-B—X-LysΨ[COCO]—O-iPropyl derivatives on solid phase (a) Teoc-Lys(Boc)Ψ[CHOHCO]—O-iPropyl Cbz-Lys(Boc)Ψ[CHOHCO]-OMe (10 g) was hydrogenated under the conditions described in example 1f to afford H-Lys(Boc)Ψ[CHOHCO]-OMe in quantitative yield. The crude product was treated with 2-(trimethylsilyl)ethoxycarbonyl hydroxy-succinimide (6.7 g) in N,N-dimethylformamide (100 mL) in the presence of N,N-diisopropylethylamine (pH=8) for 2 hours at room temperature. The reaction mixture was evaporated to dryness and the residue was dissolved in ethyl acetate and washed with 2% aqueous citric acid, water, 5% aqueous sodium hydrogencarbonate and brine. Drying over sodium sulfate and evaporation of the solvent afforded, after chromatography on silica gel (eluent: ethyl acetate/heptane=1/1 v/v), Teoc-Lys(Boc)Ψ[CHOHCO]-OMe (9.1 g). Subsequent transesterification was accomplished by adding dropwise Teoc-Lys(Boc)Ψ[CHOHCO]-OMe (2.8 g) to a stirred mixture of isopropyl alcohol (5.4 mL), THF (27.1 mL) and 1.6 M n-butyl lithium in hexane (13.6 mL) at room temperature.

After 1 hour the reaction mixture was cooled to 0° C. and glacial acetic acid (2.5 mL) was added. The reaction mixture was concentrated to a small volume and diluted with ethyl acetate, washed with water (2×) and dried over sodium sulfate. Filtration and removal of the solvent in vacuo gave the crude product. Chromatography on silica gel (eluent: ethyl acetate/heptane=1/1 v/v) afforded the title compound (2.9 g).

TLC: Rf=0.53, heptane/ethyl acetate 1/1 v/v on silica.

(b) Teoc-Lys(CO—O-methyl-resin)Ψ[CHOHCO]—O-iPropyl

Teoc-Lys(Boc)Ψ[CHOHCO]—O-iPropyl (2.8 g) was dissolved diethyl ether (36 mL) and para-toluene sulfonic acid (1.8 g) was added. After 2 hours at 30° C. the reaction mixture was evaporated and the residue was dried in vacuo to give Teoc-LysΨ[CHOHCO]—O-iPropyl. To a suspension of 4.2 g of hydroxymethyl-resin (Bachem, 1.02 mmol/g) in 50 mL of acetonitrile/dichloromethane (1/1 v/v) and triethylamine (1.81 mL) was added N,N-disuccinimidyl carbonate (3.36 g). The suspension was shaken for 2 hours at ambient temperature on an orbital shaker. The resin was filtered off and washed with dichloromethane, acetonitrile and dichloromethane (three times each) and dried. Teoc-LysΨ[CHOHCO]—O-iPropyl (see above) was dissolved in 50 mL of acetonitrile/dichloromethane (1/1 v/v). The pH of the solution was adjusted to 8 using triethylamine. This solution was added to the resin and the suspension was shaken for 16 hours at room temperature. The solvent was removed by filtration and the resin was washed according to the procedures described earlier. After drying in vacuo, 5.43 g of Teoc-Lys(CO—O-methyl-resin)Ψ[CHOHCO]—O-iPropyl was obtained.

(c) H-Lys(CO—O-methyl-resin)Ψ[CHOHCO]—O-iPropyl

A suspension of 2.5 g of Teoc-Lys(CO—O-methyl-resin)Ψ[CHOHCO]—O-iPropyl in trifluoroacetic acid/dichloromethane (50 mL, 1/9 v/v) was shaken for 45 min at room temperature. The resin was thoroughly washed with dichloromethane and dried under high vacuum to give H-Lys(CO—O-methyl-resin)Ψ[CHOHCO]—O-iPropyl (2.5 g)

(d) Boc-X-Lys(CO—O-methyl-resin)Ψ[CHOHCO]—O-iPropyl

H-Lys(CO—O-methyl-resin)Ψ[CHOHCO]—O-iPropyl was divided over 4 reactors in portions of 500 mg. The resin was washed with a 1% solution of N,N-diisopropylethylamine in dichloromethane/N,N-dimethylformamide (3/2 v/v) and dichloromethane (three times each). Next, 10 mL of dichloromethane/N,N-dimethylformamide (3/2 v/v) was added to the resin followed by building block Boc-X—OH (139 mg Boc-D-leu-OH, 139 mg Boc-Leu-OH, 148 mg Boc-Gln-OH or 159 mg Boc-Phe-OH), 2-(1H-Benzotriazol-1-yl)-1,1,3,3-tetramethyluronium tetrafluoroborate (TBTU, 193 mg) and N,N-diisopropylethylamine (105 μL). The suspension was shaken for 90 min at room temperature, whereafter the solvent was removed by filtration. The resin was washed with dichloromethane/N,N-dimethylformamide (3/2 v/v), N,N-dimethylformamide and dichloromethane (three times each) and dried.

(e) H—X-Lys(CO—O-methyl-resin)Ψ[CHOHCO]—O-iPropyl

The Boc-group of the four different X-blocks was removed under the same conditions as described for the deprotection of the Teoc-group (see example 44c) to give four times 500 mg of H—X-Lys(CO—O-methyl-resin)Ψ[CHOHCO]—O-iPropyl. This resin (500 mg) was distributed over 5 reaction vessels.

(f) EtSO$_2$-B—X-Lys(CO—O-methyl-resin)Ψ[CHOHCO]—O-iPropyl

The couplings of the second building block EtSO$_2$-B—OH (27.0 mg EtSO$_2$-Asn-OH, 26.8 mg EtSO$_2$-D-Leu-OH, 30.8 mg EtSO$_2$-D-Phe-OH, 36.8 mg EtSO$_2$-Nal-OH and 32.4 mg EtSO$_2$-D-3-Tiq-OH, prepared according to the methods as described in example 41) were performed under the same conditions as described in procedure (d), based on 100 mg resin. After work-up, the 20 reaction vessels (resulting from 4 different X blocks and 5 different B blocks) were dried in vacuo.

(g) EtSO$_2$-B—X-Lys(CO—O-methyl-resin)Ψ[COCO]—O-iPropyl

EtSO$_2$-B—X-Lys(CO—O-methyl-resin)Ψ[CHOHCO]—O-iPropyl (100 mg) was swollen in a solution of 1-hydroxy-1,2-benziodoxol-3(1H)-one 1-oxide (0.18 M) in dimethylsulfoxide (2 mL) and dichloromethane (0.2 mL). The reaction mixture was allowed to shake overnight at room temperature, whereafter the solvent was removed by filtration. Subsequent washing with dimethylsulfoxide and dichloromethane (three times each) afforded, after drying, EtSO$_2$-B—X-Lys(CO—O-methyl-resin)Ψ[COCO]-O-iPropyl.

(h) EtSO$_2$-B—X-LysΨ[COCO]—O-iPropyl

A solution of trifluoroacetic acid/thioanisole (2 mL, 10/1 v/v) was added to EtSO$_2$-B—X-Lys(CO—O-methyl-resin)Ψ[COCO]—O-iPropyl (100 mg) and the reaction mixture was shaken for 4 hours at room temperature. The resin was filtered, washed with trifluoroacetic acid (three times) whereafter the filtrate was evaporated to dryness in vacuo. The residue was rinsed with heptane (2 mL) and vigorously stirred whereafter the heptane layer was decanted. This procedure was repeated twice. The crude product was dried and directly applied on a preparative Supelcosil C18DB column (21×250 mm) for purification, using the following conditions: Flow: 20 mL/min; Buffers A: aqueous trifluoroacetic acid 0.1 M, B: water, C: acetonitrile/water 6/4 v/v; Gradient (depending on the polarity of the product) 3% A—67% B—30% C to 3% A—52% B—45% C in 40 min. UV-detection at 210 nm. The main peaks, corresponding to the desired compounds, were isolated and lyophilized to give the purified end products as depicted in table 44.

Table 44: Characterization (retention time on reversed phase HPLC and M+H peak in electrospray mass spectrometry) of EtSO$_2$-B—X-LysΨ[COCO]—O-iPropyl prepared on Hydroxymethyl-resin. HPLC conditions: Flow: 1.0 mL/min; Buffers A: water, B: acetonitrile/water (6/4 v/v), C: 0.5 M phosphate-buffer pH=2.1, Gradient: 0→45 min 65% A/15% B/20% C→0% A/80% B/20% C. UV-detection at 210 nm.

| | B | | | | |
|---|---|---|---|---|---|
| | Asn | D-Leu | D-Phe | Nal | D-3-Tig |
| EtSO$_2$-B-D-Leu-D/L-LysΨ[COCO]-O-iPropyl | Rt = 17.07 min M + H = 536.4 | Rt = 27.20 min M + H = 535.6 | Rt = 30.89 min M + H = 569.4 | Rt = 38.17 min M + H = 619.6 | Rt = 33.54 min M + H = 581.4 |
| EtSO$_2$-B-Leu-D/L-LysΨ[COCO]-O-iPropyl | Rt = 17.17 min M + H = 536.4 | Rt = 30.78 min M + H = 535.6 | Rt = 32.89 min M + H = 569.4 | Rt = 37.79 min M + H = 619.6 | Rt = 33.60 min M + H = 581.4 |
| EtSO$_2$-B-Gln-D/L-LysΨ[COCO]-O-iPropyl | Rt = 5.40 min M + H = 551.2 | Rt = 15.74 min M + H = 550.4 | Rt = 18.05 min M + H = 584.4 | Rt = 28.44 min M + H = 634.4 | Rt = 21.27 min M + H = 596.4 |
| EtSO$_2$-B-Phe-D/L-LysΨ[COCO]-O-iPropyl | Rt = 20.75 min M + H = 570.4 | Rt = 33.33 min M + H = 569.4 | Rt = 35.18 min M + H = 603.4 | Rt = 39.47 min M + H = 653.6 | Rt = 35.92 min M + H = 615.6 |

EXAMPLE 45

The following compounds can be prepared by using the methods of the present invention:

CF$_3$SO$_2$-D-Cha-Pro-LysΨ[COCO]—O-iPropyl
MeSO$_2$-D-Tyr(Me)-Pro-LysΨ[COCO]—O-iPropyl
n-ButylSO$_2$-D-Tyr(Me)-Pro-LysΨ[COCO]—O-iPropyl
CF$_3$SO$_2$-D-Tyr(Me)-Pro-LysΨ[COCO]—O-iPropyl
BzlSO$_2$-D-Tyr(Me)-Pro-LysΨ[COCO]—O-iPropyl
EtSO$_2$-D-(p-OEt-Phe)-Pro-LysΨ[COCO]—O-iPropyl
EtSO$_2$-D-Nle-Pro-LysΨ[COCO]—O-iPropyl
EtSO$_2$-D-Cha-Azt-LysΨ[COCO]—O-iPropyl
EtSO$_2$-D-Cha-(N-cyclopentyl-Gly)-LysΨ[COCO]—O-iPropyl
EtSO$_2$-D-Cha-Val-LysΨ[COCO]—O-iPropyl
EtSO$_2$-D-Cha-Pec-LysΨ[COCO]—O-iPropyl
EtSO$_2$-D-Cha-(3,4-dehydro-Pro)-LysΨ[COCO]—O-iPropyl
EtSO$_2$-D-Cha-Pro-LysΨ[COCO]-Azetidine
MeSO$_2$-D-Cha-Pro-LysΨ[COCO]-Azetidine
n-ButylSO$_2$-D-Cha-Pro-LysΨ[COCO]-Azetidine
CF$_3$SO$_2$-D-Cha-Pro-LysΨ[COCO]-Azetidine
BzlSO$_2$-D-Cha-Pro-LysΨ[COCO]-Azetidine
[3-(BzlSO$_2$amino)-2-oxo-1,2-dihydropyridinyl]-acetyl-LysΨ[COCO]-Azetidine
[3-(BzlSO$_2$amino)-6-methyl-2-oxo-1,2-dihydropyridinyl]-acetyl-LysΨ[COCO]-Azetidine
MeSO$_2$-D-Cha-Pro-AcgΨ[COCO]—O-iPropyl
n-ButylSO$_2$-D-Cha-Pro-AcgΨ[COCO]—O-iPropyl
CF$_3$SO$_2$-D-Cha-Pro-AcgΨ[COCO]—O-iPropyl
BzlSO$_2$-D-Cha-Pro-AcgΨ[COCO]—O-iPropyl
EtSO$_2$-D-Tyr(Me)-Pro-AcgΨ[COCO]—O-iPropyl
MeSO$_2$-D-Tyr(Me)-Pro-AcgΨ[COCO]—O-iPropyl
n-ButylSO$_2$-D-Tyr(Me)-Pro-AcgΨ[COCO]—O-iPropyl
CF$_3$SO$_2$-D-Tyr(Me)-Pro-AcgΨ[COCO]—O-iPropyl
BzlSO$_2$-D-Tyr(Me)-Pro-AcgΨ[COCO]—O-iPropyl
EtSO$_2$-D-Tyr(Et)-Pro-AcgΨ[COCO]—O-iPropyl
EtSO$_2$-D-Nle-Pro-AcgΨ[COCO]—O-iPropyl
EtSO$_2$-D-Cha-Azt-AcgΨ[COCO]—O-iPropyl
EtSO$_2$-D-Cha-(N-cyclopentyl-Gly)-AcgΨ[COCO]—O-iPropyl
EtSO$_2$-D-Cha-Val-AcgΨ[COCO]—O-iPropyl
EtSO$_2$-D-Cha-Pec-AcgΨ[COCO]—O-iPropyl
EtSO$_2$-D-Cha-(3,4-dehydro-Pro)-AcgΨ[COCO]—O-iPropyl
EtSO$_2$-D-Cha-Pro-AcgΨ[COCO]-Azetidine
EtSO$_2$-D-Tyr(Me)-Pro-AcgΨ[COCO]-Azetidine
EtSO$_2$-D-Tyr(Me)-Pro-AcgΨ[COCO]—NH$_2$
MeSO$_2$-D-Cha-Pro-AcgΨ[COCO]-Azetidine
n-ButylSO$_2$-D-Cha-Pro-AcgΨ[COCO]-Azetidine
CF$_3$SO$_2$-D-Cha-Pro-AcgΨ[COCO]-Azetidine
BzlSO$_2$-D-Cha-Pro-AcgΨ[COCO]-Azetidine
3-(BzlSO$_2$-amino)-1-carboxymethyl-pyridin-2-one-AcgΨ[COCO]—O-iPropyl
3-(BzlSO$_2$-amino)-1-carboxymethyl-pyridin-2-one-AcgΨ[COCO]-Azetidine
3-(BzlSO$_2$-amino)-1-carboxymethyl-6-methyl-pyridin-2-one-AcgΨ[COCO]—O-iPropyl
3-(BzlSO$_2$-amino)-1-carboxymethyl-6-methyl-pyridin-2-one-AcgΨ[COCO]-Azetidine The biological activities of the compounds of the present invention were determined by the following test methods.

I. Anti-thrombin Assay

Thrombin (Factor hIa) is a factor in the coagulation cascade.

The anti-thrombin activity of compounds of the present invention was assessed by measuring spectrophotometrically the rate of hydrolysis of the chromogenic substrate s-2238 exterted by thrombin. This assay for anti-thrombin activity in a buffer system was used to assess the IC$_{50}$-value of a test compound.

Test medium: Tromethamine-NaCl-polyethylene glycol 6000 (TNP) buffer
Reference compound: 12581 (Kabi)
Vehicle: TNP buffer.

Solubilisation can be assisted with dimethylsulfoxide, methanol, ethanol, acetonitrile or tert.-butyl alcohol which are without adverse effects in concentrations up to 2.5% in the final reaction mixture.

Technique Reagents*

1. Tromethamine-NaCl (TN) buffer
   Composition of the buffer:

| Tromethamine (Tris) | 6.057 g | (50 mmol) |
|---|---|---|
| NaCl | 5.844 g | (100 mmol) |
| Water to | 1 l | |

The pH of the solution is adjusted to 7.4 at 37° C. with HCl (10 mmol.l$^{-1}$).

2. TNP buffer
   Polyethylene glycol 6000 is dissolved in TN buffer to give a concentration of 3 g.l$^{-1}$.

3. S-2238 solution
   One vial S-2238 (25 mg; Kabi Diagnostica, Sweden) is dissolved in 20 ml TN buffer to give a concentration of 1.25 mg.ml$^{-1}$ (2 mmol.l$^{-1}$).

4. Thrombin solution
   Human thrombin (16 000 nKat.vial$^{-1}$; Centraal Laboratorium voor Bloedtransfusie, Amsterdam, The Netherlands) is dissolved in TNP buffer to give a stock solution of 835 nKat.ml$^{-1}$.
   Immediately before use this solution is diluted with TNP buffer to give a concentration of 3.34 nKat.ml$^{-1}$.

All ingredients used are of analytical grade
For aqueous solutions ultrapure water (Milli-Q quality) is used.

Preparation of Test and Reference Compound Solutions

The test and reference compounds are dissolved in Milli-Q water to give stock concentrations of $10^{-2}$ mol.l$^{-1}$. Each concentration is stepwise diluted with the vehicle to give concentrations of $10^{-1}$, $10^{-4}$ and $10^{-5}$ mol.l$^{-1}$. The dilutions, including the stock solution, are used in the assay (final concentrations in the reaction mixture: $3 \cdot 10^{-3}$; $10^{-3}$; $3 \cdot 10^{-4}$; $10^{-4}$; $3 \cdot 10^{-5}$; $10^{-5}$, $3 \cdot 10^{-6}$ and $10^{-6}$ mol.l$^{-1}$, respectively).

Procedure

At room temperature 0.075 ml and 0.025 ml test compound or reference compound solutions or vehicle are alternately pipetted into the wells of a microtiter plate and these solutions are diluted with 0.115 ml and 0.0165 ml TNP buffer, respectively. An aliquot of 0.030 ml S-2238 solution is added to each well and the plate is pre-heated and pre-incubated with shaking in an incubator (Amersham) for 10 min. at 37° C. Following pre-incubation the hydrolysis of S-2238 is started by addition of 0.030 ml thrombin solution to each well. The plate is incubated (with shaking for 30 s) at 37° C.. Starting after 1 min of incubation, the absorbance of each sample at 405 nm is measured every 2 min. for a period of 90 min. using a kinetic microtiter plate reader (Twinreader plus, Flow Laboratories).

All data are collected in an IBM personal computer using LOTUS-MEASURE. For each compound concentration (expressed in mol.l$^{-1}$ reaction mixture) and for the blank the absorbance is plotted versus the reaction time in min.

Evaluation of responses: For each final concentration the maximum absorbance was calculated from the assay plot. The IC$_{50}$-value (final concentration, expressed in $\mu$mol.l$^{-1}$, causing 50% inhibition of the maximum absorbance of the blank) was calculated using the logit transformation analysis according to Hafner et al. (Arzneim.-Forsch./Drug Res. 1977, 27(II): 1871–3).

IC$_{50}$-values of compounds of the present invention are given in the following Table.

Antithrombin Activity

| Example | IC$_{50}$ ($\mu$mol-l$^{-1}$) |
|---|---|
| 4 | 0.09 |
| 24 | 0.01 |
| 38 | 0.11 |
| 40 | 0.02 |

II. Anti-factor Xa Assay

Activated Factor X (Xa) is a factor in the coagulation cascade. The anti-Xa activity of compounds of the present invention was assessed by measuring spectrophotometrically the rate of hydrolysis of the chromogenic substrate s-2222 exterted by Xa. This assay for anti-Xa activity in a buffer system was used to assess the IC$_{50}$-value of the test compound.

In general the followed procedure and test conditions were analogous to those of the anti-thrombin assay as described above. Differences are indicated below.

Reference compound: benzamidine
Vehicle: TNP buffer.

Solubilisation can be assisted with dimethylsulfoxide, methanol, ethanol, acetonitrile or tert.-butyl alcohol which are without adverse effects in concentrations up to 1% (for DMSO) and 2.5% (for the other solvents) in the final reaction mixture.

Technique Reagents*
3. S-2222 solution
    One vial S-2222 (15 mg; Kabi Diagnostica, Sweden) is dissolved in 10 ml water to give a concentration of 1.5 mg.ml$^{-1}$ (2 mmol.l$^{-1}$).
4. Xa solution
    Bovine Factor Xa Human (71 nKat.vial$^{-1}$, Kabi Diagnostica) is dissolved in 10 ml TNP buffer and then further diluted with 30 ml TNP buffer to give a concentration of 1.77 nKat.ml$^{-1}$. The dilution has to be freshly prepared.

Procedure

Instead of the S-2238 solution (in anti-thrombin assay), the above S-2222 solution is added to each well in this assay.

Anti-factor Xa Activity

| Example | IC$_{50}$ ($\mu$mol-l$^{-1}$) |
|---|---|
| 1 | 0.64 |
| 5 | 0.28 |
| 28 | 0.02 |

III. Anti Factor VIIa/Tissue Factor Assay

Vascular damage initiates a series of enzyme generation reactions ultimately leading to the formation of a fibrin gel at the site of the injury. The primary enzyme generation reaction is the generation of activated factor VII (VIIa) from proenzyme factor VII. This activation reaction takes place by an as yet unknown mechanism. One hypothesis is that small amounts of factor Xa present in plasma, bind to the membrane-bound protein Tissue Factor (TF)—a protein which normally does not contact blood but which gets exposed to it by injury—and that this complex of membrane-bound TF and factor Xa activates factor VII (ref. 1). The activated Factor VII then also binds to membrane-bound TF and this intrinsic tenase complex next converts Factor X into Factor Xa.

Thrombosis develops when there is insufficient control of the coagulation reaction. One way to restore this control is by inhibiting essential coagulation enzymes such as for instance the complex of membrane-bound TF and Factor VIIa. Since inhibitors of VIIa or the VIIa/TF complex most likely will also inhibit the tenase complex, inhibitors of the latter complex may also be found by determining the inhibition of VIIa or VIIa/TF by test compounds. A method is described by which the inhibitory potency of compounds towards VIIa/TF complex can be established. Test compounds are mixed at various concentrations with factor VIIa and TF and with a chromogenic substrate, which is known to be split far better by TF-bound VIIa than by free VIIa. The amidolytic reaction taking place is continuously monitored in a microtiter plate reader. Inhibitory potency of the compounds investigated is expressed by the IC$_{50}$, defined as the concentration of compounds yielding 50% inhibition of the amidolytic reaction, ninety minutes after the start of the reaction.

Reagents

Hepes Buffer

A ten times concentrated Hepes buffer made by dissolving 29.40 g CaCl$_2$.2H$_2$O, 47.66 g Hepes, 87.66 g NaCl and 30.00 g polyethyleneglycol (PEG) MW=6000 in 1000 ml aqua bidest. After the solution has been heated to 37° C., the pH of the buffer is set on 7.40 with help of 10 molar NaOH. The concentrated buffer solution is stored at 4° C. and is stable for at least two months at this condition. Prior to use the buffer is diluted in aqua bidest. 1 to 8 to obtain a final concentration in the wells (See test procedure) of 20 mM $CaCl_2$, 20 mM Hepes, 150 mM NaCl and 0.3% PEG6000. If compounds are dissolved and diluted in aqua bidest. or another vehicle because of an insufficient solubility the Hepes buffer can be diluted 1 to 6 to preserve the same ionic strength in the test.

Recombinant Human Factor VIIa

Recombinant human factor VIIa is obtained from American Diagnostica Inc, Greenwich, Conn. Each vial contains 1.2 mg recombinant human factor VIIa, which is lyophilized from 2 ml buffer composed of 10 mM glycylglycine, 50 mM NaCl, 10 mM $CaCl_2$, 30 mg/ml mannitol, 0.1% Tween, pH 5.5. The contents of each of these vials is reconstituted with 2 ml aqua bidest. as indicated by the manufacturer. The 2 ml $1.2*10^{-5}$ stock solution thus obtained is divided in smaller fractions, which are stored at −30° C. At this condition these VIIa samples are stable for at least 6 months.

Recombinant Human Tissue Factor

Recombinant human Tissue Factor is obtained from American Diagnostica Inc, Greenwich, Conn. Each vial contains 25 µg recombinant human Tissue Factor (non-lipidated, MW 35000 Dalton), which is lyophilized from 1 ml Tris/HCl buffer (pH 8.0) composed of 150 mM NaCl, 200 mM mannitol and 10 mM CHAPS (Steroid derivative used to solubilize membrane proteins; see Merck Index). The contents of each vial is reconstituted with 1 ml aqua bidest. as indicated by the manufacturer. The 1 ml $7.14\times10^{-7}$ M stock solution thus obtained is divided in smaller fractions, which are stored at −30° C. Thus stored these VIIa samples are stable for at least 67 months.

Pefachrome VIIa

Pefachrome VIIa—$CH_3SO_2$-D-Cha-but-Arg-pNa.AcOH (MW 670.8)—is obtained from Pentapharm Ltd, Basle, Switzerland, in vials containing 10 µmol of this chromogenic substrate. At the day of the experiment the contents of a vial are dissloved in 8.33 ml aqua bidest., yielding a 1.2 mMolar Pefachrome VIIa solution. What remains of this solution is stored at −30° C. and is stable for at least 6 months at this condition.

Recombinant TF/Recombinant VIIa Solution

At the day of the experiment a deep frozen sample of $1.2*10^{-5}$ M recombinant VIIa and a deep frozen sample of recombinant human tissue factor of $7.14*10^{-7}$ is defrosted. The defrosted $7.14*10^{-7}$ solution of recombinant human TF is diluted to $4*10^{-7}$ M and 30 µl of this solution is mixed with 1 µl of the defrosted recombinant VIIa solution of $1.2*1$ 5 and with 449 µl Hepes buffer, yielding a Hepes buffer solution containing 25 nM recombinant VIIa and 25 nM recombinant TF. The amount of 480 µl TF/VIIa solution is sufficient to examine the inhibition of eight solutions of one test compound. N times this amount is needed to establish the $IC_{50}$ of N test compounds.

Preparation of Test Compounds

Test compounds are dissolved in Hepes buffer to give $5*10^{-3}$ stock solutions (A). From this solution seven additional solutions with concentrations of $1.67*10^{-3}$ M (B), $5.56*10^{-4}$ M (C), $1.85*10^{-4}$ M (D), $6.17*10^{-5}$ M (E), $2.06*10^{-5}$ M (F), $6.86*10^{-4}$ M (G) and $2.29*10^{-4}$ M (H) are prepared by diluting each foregoing solution with a factor three in Hepes buffer. Such a series of solutions is prepared for the reference compound Org 34593 and also for each of the N-1 test compounds. If considered more convenient, other sets of solutions with different compound concentrations may be prepared.

Procedure

Compounds are distributed column by column over the microtiter plate and one column of eight wells is reserved for a series of uninhibited reactions. Hundred µl of Hepes buffer is brought into all (N+1)*8 wells with an eight channel pipette. Here N is the number of different test compounds, including the reference compound Org 34593. Hereafter, fifty µl of the pefachrome VIIa solution of 1.2 mM is added with an eight channel pipette to the 100 µl Hepes buffer in all of the (N+1)*8 wells reserved for compound testing and the blank reactions. Then 50 µl of each of the eight solutions of the first, second, third up to the N-th compound is mixed in a descending order of concentrations with the contents of the first (A) until the eighth well (H) of columns 1, 2, 3, up to N respectively, so as to obtain a one compound per column distribution with a from top to bottom descending order of compound concentrations per column. Finally 50 µl Hepes buffer is added to the eight wells of the N+1 th column reserved for a series of blanks.

After the whole plate has been prepared it is shaken for 1 minute in a microtiter plate shaker incubator (Amersham) and the solutions are brought to 37° C. by incubating the plate in the same instrument for 10 minutes.

The reactions are initiated by adding 50 µl of the 25 nM VIIa/25 nM TF solution, which is preheated at 37° C., to each of the (N+1)*8 wells with help of an eight channel pipette. After the plate is shaken for 30 seconds it is placed in a thermostated microtiter plate reader and the 405 nm absorbance is read in each well at time intervals of 1 minute during 90 minutes. Absorbances are collected in LOTUS 1.2.3, loaded into a PC connected to the kinetic reader.

Evaluation

The (end-)absorbances measured at 90 minutes are corrected for the blank absorbances at the beginning of the test by subtraction of the corresponding first absorbance value measured 1 minute after the initiation of the reaction. The corrected end absorbances in the presence (Abs[I]) and absence (Abs[O]) of the test compound are converted into logit values by calculating $+\log((Abs[O]/Abs[I])-1)$ for each concentration [I] of the test compound. These logit values are plotted against the −log of concentrations of the test compound. Such a logit plot usually displays a linear relationship between 20% and 80% inhibition of the end-absorbance.

The $pIC_{50}$ value is defined as the −log (concentration in M) od the test compound for which the logit value is equal to zero. This value is calculated by linear regression of the logit vs −log [I] relation preferably around the logit zero value. When the compound tested is so active towards VIIa/TF that the $pIC_{50}$ must be calculated by extrapolation instead of interpolation, it is best to prepare an additional set of dilutions of this test compound and to perform the assay again. This method of calculating a $pIC_{50}$ value is described by Hafner et al. (ref. 2). The corresponding $IC_{50}$ is calculated as $10^{-pI50}$ and is expressed in Molar.

Quantity Required

About one mg is required to assess the $IC_{50}$ of a test compound.

Reference Compound

As a reference compound Org 34593 (PPACK) may be used. For this compound an $IC_{50}$ of $3*10^{-7}$ M has been established.

References (1) The structural biology of expression and function of Tissue Factor: Edgington, T. S., et al. in Thrombosis and Haemostasis 66(1), 67–79 (1991).

(2) Mathematical analysis of concentration response relationships: Hafner, D. et al. in Arzneim. Forsch./Drug Research 27, 1871–1873 (1977).

As a single point measurement of the anti factor VIIa/tissue factor activity of compounds of the present invention, the percentage of inhibition at a concentration of $1 \times 10^{-5}$ M is given in the following Table. For the determination of the percentages, procedures as described above were followed.

Anti, factor VIIa/tissue factor activity (percentage inhibition at a concentration of $1 \times 10^{-5}$ M):

| Example | percentage inhibition (%) |
|---|---|
| 44) EtSO$_2$-D-Phe-Leu-LysΨ[COCO]-O-iPropyl | 98 |
| 44) EtSO$_2$-Asn-Leu-LysΨ[COCO]-O-iPropyl | 56 |
| 44) EtSO$_2$-D-3-Tiq-Phe-LysΨ[COCO]-O-iPropyl | 91 |
| 44) EtSO$_2$-D-Leu-Gln-LysΨ[COCO]-O-iPropyl | 94 |

What is claimed is:

1. A compound having the formula I $$R^1SO_2\text{—}B\text{—}X\text{—}Z\text{—}C(O)\text{—}Y \qquad (I)$$

wherein $R^1$ is $R^2OOC\text{—}(CHR^2)_m\text{—}$ or $R^2NH\text{—}CO\text{—}(CHR^2)_m\text{—}$ or is selected from (1–12C)alkyl, (2–12C)alkenyl, which groups may optionally be substituted with (3–8C)cycloalkyl, (1–6C)alkoxy, OH, COOR$^2$, CF$_3$ or halogen, and from (6–14C)aryl, (7–15C)aralkyl and (8–16C)aralkenyl, the aryl groups of which may optionally be substituted with (1–6C)alkyl, (3–8C)cycloalkyl, (1–6C)alkoxy, OH, COOH, CF$_3$ or halogen;

m is 1, 2 or 3;

each group $R^2$ is independently H, (1–12C)alkyl, (3–8C)cycloalkyl, (6–14C)aryl or (7–15C)aralkyl, the aryl groups of which may be substituted with (1–6C)alkyl, (1–6C)alkoxy or halogen;

B is a bond, an amino-acid of the formula —NH—CH[(CH$_2$)$_p$C(O)OH]—C(O)— or an ester derivative thereof wherein p is 1, 2 or 3, Gly, D-Atc, Aic, or a L- or D-amino acid having a hydrophobic, basic or neutral side chain;

X is an L-amino acid with a hydrophobic side chain, serine, threonine, a cyclic amino acid optionally having an additional heteroatom selected from N, O or S, and optionally substituted with (1–6C)alkyl, (1–6C)alkoxy, benzyloxy or oxo, or X is 2-amino-isobutyric acid, —NR$^2$—CH$_2$—C(O)— or the fragment

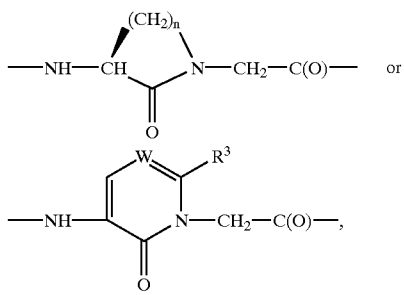

wherein n is 2, 3, or 4, W is CH or N and R$^3$ is H or (1–6C)alkyl;

Z is lysine or 4-aminocyclohexylglycine;

Y is —NH-(1–6C)alkylene-C$_6$H$_5$, the phenyl group of which may be substituted with (1–6C)alkyl, (1–6C)alkoxy or halogen, or Y is —OR$^4$ or —NR$^5$R$^6$, wherein R$^4$ is H, (2–6C)alkyl or benzyl, and R$^5$ and R$^6$ are independently H or (1–6C)alkyl or R$^5$ and R$^6$ together are (3–6C)alkylene;

or a prodrug thereof, which after administration are metabolized into the active compounds, or a pharmaceutically acceptable salt thereof.

2. The compound of claim 1, wherein Z is lysine.

3. The compound of claim 1, wherein X is a cyclic amino acid, an L-amino acid with a hydrophobic side chain, serine, threonine, —NR$^2$—CH$_2$—C(O)—, or the fragment

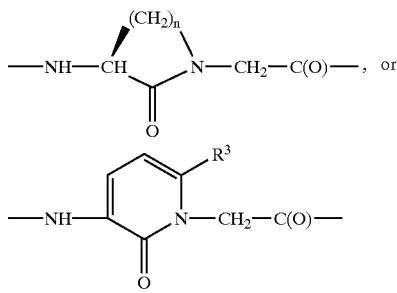

wherein R$^3$ is H, (1–6C)alkyl.

4. The compound of claim 1, wherein X is proline, leucine, threonine, phenylalanine, —NR$^2$—CH$_2$—C(O)— wherein R$^2$ is methyl, cyclopentyl or cyclohexyl, or the fragment

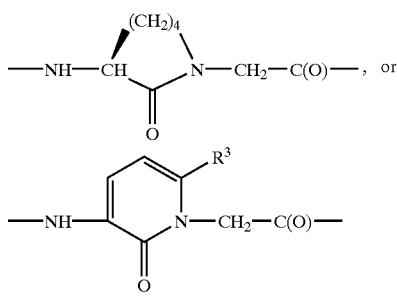

wherein R$^3$ is H or methyl.

5. The compound of claim 1, wherein B is a bond, a D-amino acid having a hydrophobic or neutral side chain.

6. The compound of claim 1, wherein R$^1$ is (1–6C)alkyl or benzyl.

7. The compound of claim 1, wherein Y is —OCH(CH$_3$)$_2$.

8. A pharmaceutical composition, comprising:

an effective amount of a compound of claim 1 and pharmaceutically suitable auxiliaries.

9. A process for preparing a pharmaceutical composition, comprising:

mixing together a compound of claim 1 with pharmaceutically acceptable auxiliaries.

10. A method of treating thrombin-related diseases in a patient in need thereof, comprising:

administering to the patient an effective amount of a compound according to claim 1.

* * * * *

UNITED STATES PATENT AND TRADEMARK OFFICE
CERTIFICATE OF CORRECTION

PATENT NO. : 6,534,495 B1
DATED : March 18, 2003
INVENTOR(S) : Anton Egbert Peter Adang It is certified that error appears in the above-identified patent and that said Letters Patent is hereby corrected as shown below:

<u>Title page,</u>
Item [73], should read:
-- Akzo Nobel, Arnhem (NL) --

Signed and Sealed this

Twenty-second Day of July, 2003

JAMES E. ROGAN
*Director of the United States Patent and Trademark Office*